US012691169B2

(12) United States Patent
Allen et al.

(10) Patent No.: US 12,691,169 B2
(45) Date of Patent: Jul. 28, 2026

(54) BROADLY REACTIVE VIRAL ANTIGENS AS IMMUNOGENS, COMPOSITIONS AND METHODS OF USE THEREOF

(71) Applicant: University of Georgia Research Foundation, Inc., Athens, GA (US)

(72) Inventors: James Allen, Athens, GA (US); Zachary Beau Reneer, Athens, GA (US); Ivette Nunez, Athens, GA (US); Hyesun Jang, Athens, GA (US); Michael Carlock, Athens, GA (US); Amanda Skarlupka, Athens, GA (US); Ted Ross, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 1055 days.

(21) Appl. No.: 17/791,861

(22) PCT Filed: Jan. 8, 2021

(86) PCT No.: PCT/US2021/012695
§ 371 (c)(1),
(2) Date: Jul. 8, 2022

(87) PCT Pub. No.: WO2021/142256
PCT Pub. Date: Jul. 15, 2021

(65) Prior Publication Data
US 2023/0055468 A1     Feb. 23, 2023

Related U.S. Application Data

(60) Provisional application No. 62/959,404, filed on Jan. 10, 2020.

(51) Int. Cl.
| | |
|---|---|
| *A61K 39/145* | (2006.01) |
| *A61P 31/16* | (2006.01) |
| *C12N 15/09* | (2006.01) |

(52) U.S. Cl.
CPC ............ *A61K 39/145* (2013.01); *A61P 31/16* (2018.01); *C12N 15/09* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 5,662,907 A | 9/1997 | Kubo et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,239,116 B1 | 5/2001 | Krieg et al. |
| 6,339,068 B1 | 1/2002 | Krieg et al. |
| 6,406,705 B1 | 6/2002 | Davis et al. |
| 6,429,199 B1 | 8/2002 | Krieg et al. |
| 2002/0106798 A1 | 8/2002 | Robinson et al. |
| 2015/0030628 A1 | 1/2015 | Ross et al. |
| 2016/0052997 A1 | 2/2016 | Hong et al. |

FOREIGN PATENT DOCUMENTS

| | | | |
|---|---|---|---|
| WO | WO/17/191258 | * | 11/2017 |
| WO | 2019124557 A1 | | 6/2019 |

OTHER PUBLICATIONS

GenBank Accession AAY28987, hemagglutinin [Influenza A virus (A/Canada/720/2005(H2N2))], May 10, 2005.*
GenBank Accession ABN50602, hemagglutinin [Influenza B virus (B/Texas/37/1988)], Feb. 14, 2007.*
GenBank Accession ALT66860, hemagglutinin [Influenza A virus (A/Bushehr/89073/2015(H1N1))], 2015.*
GenBank Accession AAQ10341, neuraminidase [Influenza A virus (A/Buenos Aires/32/96(H3N2))], 2012.*
GenBank Accession KU242426, influienza A virus (A/Bushehr/89073/2015(H1N1))] segment 4 HA gene complete cds, 2015.*
International Search Report and Written Opinion mailed Jun. 30, 2021 in corresponding International PCT Patent Application No. PCT/US2021/012695 (13 pages).
Abdel-Ghafar et al., "Update on Avian Influenza A (H5N1) Virus Infection in Humans," The New England Journal of Medicine, Jan. 17, 2008, vol. 358, No. 3, pp. 261-273.
Altschul et al., "Basic Local Alignment Search Tool," Journal of Molecular Biology, 1990, vol. 215, pp. 403-410.
Altschul et al., "Issues in searching molecular sequence databases," Nature Genetics, Feb. 1994, vol. 6, pp. 119-129.
Benton et al., "Screening λgt Recombinant Clones by Hybridization to Single Plaques in Situ," Science, Apr. 8, 1977, vol. 196, pp. 180-182.

(Continued)

*Primary Examiner* — Benjamin P Blumel
(74) *Attorney, Agent, or Firm* — Greenberg Traurig, LLP; Melissa Hunter-Ensor; Leslie Serunian

(57)     ABSTRACT

Provided herein are non-naturally occurring, broadly reactive antigens derived from influenza viruses or avian infectious bronchitis virus (IBV) that are immunogenic and capable of eliciting a broadly reactive immune response, e.g., a broadly reactive neutralizing antibody response, directed against influenza virus antigens or IBV antigens following introduction into a subject. Also provided are non-naturally, broadly reactive immunogens, vaccines, virus-like particles (VLPs) and compositions comprising the immunogens and vaccines. Methods of generating an immune response in a human or non-human subject by administering the immunogens, vaccines, VLPs, or compositions thereof are provided. In particular, the immunogens comprise broadly reactive hemagglutinin (HA) protein antigens of influenza virus strains, such as H1, H2, H3, H5, or H7, or of IBV. The immunogens also comprise broadly reactive viral neuraminidase (NA) protein antigens.

34 Claims, 4 Drawing Sheets
Specification includes a Sequence Listing.

(56)          References Cited

OTHER PUBLICATIONS

Bright et al., "Adamantane Resistance Among Influenza A Viruses Isolated Early During the 2005-2006 Influenza Season in the United States," JAMA, Feb. 22, 2006, vol. 295, No. 8, pp. 891-894.

Bright et al., "Impact of glycosylation on the immunogenicity of a DNA-based influenza H5 HA vaccine," Virology, 2003, vol. 308, pp. 270-278.

Bright et al., "Incidence of adamantane resistance among influenza A (H3N2) viruses isolated worldwide from 1994 to 2005: a cause for concern," The Lancet, Oct. 1, 2005, vol. 366, pp. 1175-1181.

Cao et al., "Cytokine Gene Transfer in Cancer Therapy," Stem Cells, 1998, vol. 16, Suppl. 1, pp. 251-260.

Corpet, Florence, "Multiple sequence alignment with hierarchical clustering," Nucleic Acids Research, 1988, vol. 16, No. 22, pp. 10881-10890.

Couzens et al., "An optimized enzyme-linked lectin assay to measure influenza A virus neuraminidase inhibition antibody titers in human sera," Journal of Virological Methods, 2014, vol. 210, pp. 7-14.

Deres et al., "In vivo priming of virus-specific cytotoxic T lymphocytes with synthetic lipopeptide vaccine," Nature, Nov. 30, 1989, vol. 342, pp. 561-564.

Ekiert et al., "A Highly Conserved Neutralizing Epitope on Group 2 Influenza A Viruses," Science, Aug. 12, 2011, vol. 333, pp. 843-850.

Garcia-Sastre et al., "Influenza A Virus Lacking the NS1 Gene Replicates in Interferon-Deficient Systems," Virology, 1998, vol. 252, Article No. VY989508, pp. 324-330.

Gillim-Ross et al., "Emerging Respiratory Viruses: Challenges and Vaccine Strategies," Clinical Microbiology Reviews, Oct. 2006, vol. 19, No. 4, pp. 614-636.

Green et al., "C3d enhancement of neutralizing antibodies to measles hemagglutinin," Vaccine, 2002, vol. 20, pp. 242-248.

Grunstein et al., "Colony hybridization: A method for the isolation of cloned DNAs that contain a specific gene," Proceedings of the National Academy of Sciences of the United States of America, Oct. 1975, vol. 72, No. 10, pp. 8961-3965.

Higgins et al., "CLUSTAL: a package for performing multiple sequence alignment on a microcomputer," Gene, 1988, vol. 73, pp. 237-244.

Higgins et al., "Fast and sensitive multiple sequence alignments on a microcomputer," Bioinformatics, 1989, vol. 5, No. 2, pp. 151-153.

Horimoto et al., "Pandemic Threat Posed by Avian Influenza A Viruses," Clinical Microbiology Reviews, Jan. 2001, vol. 14, No. 1, pp. 129-149.

Kimmel, Alan R., "[54] Identification and Characterization of Specific Clones: Strategy for Confirming the Validity of Presumptive Clones," Methods in Enzymology, 1987, vol. 152, pp. 507-511.

Klucker et al., "AF03, An Alternative Squalene Emulsion-Based Vaccine Adjuvant Prepared by a Phase Inversion Temperature Method," Journal of Pharmaceutical Sciences, Dec. 2012, vol. 101, No. 12, pp. 4490-4500.

Krug et al., "Expression and Replication of the Influenza Virus Genome," The Influenza Viruses, 1989, Chapter 2, pp. 89-152.

Kuiper et al., "B7.1 and Cytokines: Synergy in Cancer Gene Therapy," Advances in Experimental Medicine and Biology, 2000, vol. 465, pp. 381-390.

Lotze et al., "Interleukin-2: Developing Additional Cytokine Gene Therapies Using Fibroblasts or Dendritic Cells to Enhance Tumor Immunity," The Cancer Journal from Scientific American, Feb. 2000, vol. 6, Suppl. 1, pp. S61-S66.

Marsh et al., "Highly Conserved Regions of Influenza A Virus Polymerase Gene Segments Are Critical for Efficient Viral RNA Packaging," Journal of Virology, Mar. 2008, vol. 82, No. 5, pp. 2295-2304.

Mitchell et al., "Induction of heterosubtypic immunity to influenza A virus using a DNA vaccine expressing hemagglutinin-C3d fusion proteins," Vaccine, 2003, vol. 21, Nos. 9-10, pp. 902-914.

Needleman et al., "A General Method Applicable to the Search for Similarities in the Amino Acid Sequence of Two Proteins," Journal of Molecular Biology, 1970, vol. 48, pp. 443-453.

Pearson et al., "Improved tools for biological sequence comparison," Proceedings of the National Academy of Sciences of the United States of America, Apr. 1988, vol. 85, pp. 2444-2448.

Pinto et al., "Influenza Virus M2 Protein Has Ion Channel Activity," Cell, May 1, 1992, vol. 69, pp. 517-528.

Richardson et al., "NS2 protein of influenza virus is found in purified virus and phosphorylated in infected cells," Archives of Virology, 1991, vol. 116, pp. 69-80.

Ross et al., "C3d enhancement of antibodies to hemagglutinin accelerates protection against influenza virus challenge," Nature Immunology, Aug. 2000, vol. 1, No. 2, pp. 127-131.

Salgaller et al., "Use of Cellular and Cytokine Adjuvants in the Immunotherapy of Cancer," Journal of Surgical Oncology, 1998, vol. 68, pp. 122-138.

Smith et al., "Comparison of Biosequences," Advances in Applied Mathematics, 1981, vol. 2, pp. 482-489.

Tharakaraman et al., "Broadly Neutralizing Influenza Hemagglutinin Stem-Specific Antibody CR8020 Targets Residues that Are Prone to Escape due to Host Selection Pressure," Cell Host & Microbe, May 14, 2014, vol. 15, pp. 644-651.

Wahl et al., "[43] Molecular Hybridization of Immobilized Nucleic Acids: Theoretical Concepts and Practical Considerations," Methods in Enzymology, 1987, vol. 152, pp. 399-407.

Ward et al., "Expression and analysis of the NS2 protein of influenza A virus," Archives of Virology, 1995, vol. 140, pp. 2067-2073.

Yasuda et al., "Molecular Assembly of Influenza Virus: Association of the NS2 Protein with Virion Matrix," Virology, 1993, vol. 196, pp. 249-255.

Zebedee et al., "Influenza A Virus M2 Protein: Monoclonal Antibody Restriction of Virus Growth and Detection of M2 in Virions," Journal of Virology, Aug. 1988, vol. 62, No. 8, pp. 2762-2772.

* cited by examiner

MKAILVVLLYTFTTANADTLCIGYHANNSTDTVDTVLEKNVTVTHSVNLLEDKHNGK
LCKLRGVAPLHLGKCNIAGWILGNPECESLSTASSWSYIVETSNSDNGTCYPGDFIN
YEELREQLSSVSSFERFEIFPKTSSWPNHDSNKGVTAACPHAGAKSFYKNLIWLVK
KGNSYPKLNQSYINDKGKEVLVLWGIHHPSTTADQQSLYQNADAYVFVGTSRYSK
KFKPEIATRPKVRDQEGRMNYYWTLVEPGDKITFEATGNLVVPRYAFTMERNAGS
GIIISDTPVHDCNTTCQTPEGAINTSLPFQNVHPITIGKCPKYVKSTKLRLATGLRNVP
SIQSRGLFGAIAGFIEGGWTGMVDGWYGYHHQNEQGSGYAADLKSTQNAIDKITN
KVNSVIEKMNTQFTAVGKEFNHLEKRIENLNKKVDDGFLDIWTYNAELLVLLENERT
LDYHDSNVKNLYEKVRNQLKNNAKEIGNGCFEFYHKCDNTCMESVKNGTYDYPKY
SEEAKLNREKIDGVKLESTRIYQILAIYSTVASSLVLVVSLGAISFWMCSNGSLQCRIC
I

MAIIYLILLFTAVRGDQICIGYHANNSTEKVDTILERNVTVTHAKDILEKTHNGKLCKLN
GIPPLELGDCSIAGWLLGNPECDRLLSVPEWSYIMEKENPRDGLCYPGSFNDYEEL
KHLLSSVKHFEKVKILPKDRWTQHTTTGGSRACAVSGKPSFFRNMVWLTKKGSNY
PVAKGSYNNTSGEQMLIIWGVHHPNDETEQRTLYQNVGTYVSVGTSTLNKRSTPEI
ATRPKVNGQGGRMEFSWTLLDMWDTINFESTGNLIAPEYGFKISKRGSSGIMKTEG
TLENCETKCQTPLGAINTTLPFHNIHPLTIGECPKYVKSERLVLATGLRNVPQIESRG
LFGAIAGFIEGGWQGMVDGWYGYHHSNDQGSGYAADKESTQKAIDGITNKVNSVI
EKMNTQFEAVGKEFNNLERRLENLNKKMEDGFLDVWTYNAELLVLMENERTLDFH
DSNVKNLYDKVRMQLRDNAKELGNGCFEFYHKCDDECMNSVKNGTYDYPKYEEE
SKLNRNEIKGVKLSNMGVYQILAIYATVAGSLSLAIMIAGISFWMCSNGSLQCRICI

MKTIIALSYILCLVFAQKIPGNDNSTATLCLGHHAVPNGTIVKTITNDRIEVTNATELVQ
NSSIGEICDSPHQILDGENCTLIDALLGDPQCDGFQNKKWDLFVERSKAYSNCYPY
DVPD
YASLRSLVASSGTLEFNNESFNWTGVTQNGTSSACIRRSSSSFFSRLNWLTHLNYT
YPALNVTMPNNEQFDKLYIWGVHHPGTDKDQIFLYAQSSGRITVSTKRSQQAVIPNI
GSRP
RIRDIPSRISIYWTIVKPGDILLINSTGNLIAPRGYFKIRSGKSSIMRSDAPIGKCKSECI
TPNGSIPNDKPFQNVNRITYGACPRYVKQSTLKLATGMRNVPEKQTRGIFGAIAGFI
ENGWEGMVDGWYGFRHQNSEGRGQAADLKSTQAAIDQINGKLNRLIGKTNEKFH
QIEKEFSEVEGRIQDLEKYVEDTKIDLWSYNAELLVALENQHTIDLTDSEMNKLFEKT
KKQLRENAEDMGNGCFKIYHKCDNACIGSIRNGTYDHNVYRDEALNNRFQIKGVEL
KSGYKDWILWISFAISCFLLCVALLGFIMWACQKGNIRCNICI

IAN3

MEKIVLPFAVISLVKSDQICIGYHANNSTEQVDTIMEKNVTVTHAQDILEKTHNGKLC
DLNGVKPLILKDCSVAGWLLGNPMCDEFIRVPEWSYIVERANPANDLCYPGNLNDY
EELKHLLSRINHFEKTLIIPKSSWPNHETSLGVSAACPYQGTPSFFRNVVWLIKKND
AYPTIKISYNNTNREDLLILWGIHHSNNAAEQTNLYKNPTTYVSVGTSTLNQRLVPKI
ATRSQVNGQRGRMDFFWTILKPNDAIHFESNGNFIAPEYAYKIVKKGDSTIMKSEVE
YGHCNTKCQTPIGAINSSMPFHNIHPLTIGECPKYVKSNKLVLATGLRNSPLNVPQR
ETRGLFGAIAGFIEGGWQGMVDGWYGYHHSNEQGSGYAADKESTQKAIDGITNKV
NSIIDKMNTQFEAVGKEFNNLERRIENLNKKMEDGFLDVWTYNAELLVLMENERTL
DFHDSNVKNLYDKVRLQLRDNAKELGNGCFEFYHKCDNECMESVRNGTYDYPQY
SEEARLNREEISGVKLESMGTYQILSIYSTVASSLALAIMIAGLSFWMCSNGSLQCRI
CI

Q6
MNTQILALVACMLIGVKGDKICLGHHAVSNGTKVNTLTERGVEVVNATETVERTNIP
RICSKGKRTVDLGQCGLLGTITGPPQCDQFLEFSADLIIERREGTDVCYPGKFVNEE
ALRQILRESGGIDKESMGFTYSGIRTNGATSACRRSGSSFYAEMKWLLSNTDNAAF
PQMTKSYKNTRKKPALIIWGIHHSGSTTEQTKLYGSGNKLITVGSSNYQQSFVPSP
GARPQVNGQSGRIDFHWLMLNPNDTVTFSFNGAFIAPDRASFLRGKSMGIQSGVQ
VDANCEGDCYHSGGTIISNLPFQNINSRAVGKCPRYVKQESLLLATGMKNVPEIPK
GRGLFGAIAGFIENGWEGLIDGWYGFRHQNAQGEGTAADYKSTQSAIDQITGKLNR
LIEKTNQQFELIDNEFNEVEKQIGNVINWTRDSMTEVWSYNAELLVAMENQHTIDLA
DSEMNKLYERVKRQLRENAEEDGTGCFEIFHKCDDDCMASIRNNTYDHSKYREEA
MQNRIQIDPVKLSSGYKDVILWFSFGASCFILLAIAMGLVFICVKNGNMRCTICI

FIG. 1F

IBV HA

B14
MKAIIVLLMVVTSNADRICTGITSSNSPHVVKTATQGEVNVTGVIPLTTTPTKSHFAN
LKGTKTRGKLCPKCLNCTDLDVALGRPKCMGTIPSAKASILHEVRPVTSGCFPIMHD
RTKIRQLPNLLRGYEKIRLSTHNVINAEKAPGGPYRIGTSGSCPNITNGNGFFATMA
WAVPDNNKTATNPLTVEVPYICTEGEDQITVWGFHSDNETQMKKLYGDSKPQKFT
SSANGVTTHYVSQIGGFPNQTEDGGLPQSGRIVVDYMVQKSGKTGTIVYQRGILLP
QKVVWCASGRSKVIKGSLPLIGEADCLHEKYGGLNKSKPYYTGEHAKAIGNCPIVVK
TPLKLANGTKYRPPAKLLKERGFFGAIAGFLEGGWEGMIAGWHGYTSHGAHGVAV
AADLKSTQEAINKITKNLNSLSELEVKNLQRLSGAMDELHNEILELDEKVDDLRADTI
SSQIELAVLLSNEGIINSEDEHLLALERKLKKMLGPSAVDIGNGCFETKHKCNQTCLD
RIAAGTFNAGEFSLPTFDSLNITAASLNDDGLDNHTILLYYSTAASSLAVTLMIAIFIVY
MVSRDNVSCSICL

NA-D
MNPNQKIITIGSICMAIGIISLILQIGNIISIVVVSHSIQTGSQNHTGICNQRIITYENSTVV
NQTYVNISNTNVVAGKDVTSVTLAGNSSLCPISGWAIYSKDNSIRIGSKGDVFVIREP
FISCSHLECRTFFLTQGALLNDKHSNGTVKDRSPYRALMSCPIGEAPSPYNSRFES
VAWSASACHDGMGWLTIGISGPDNGAVAVLKYNGIITETIKSWRKNILRTQESECVC
VNGSCFTIMTDGPSDGQASYKIFKIEKGKITKSIELNAPNYHYEECSCYPDTGTVMC
VCRDNWHGSNRPWVSFNQNLDYQIGYICSGVFGDNPRPKDGTGSCGPVTVDGAN
GVKGFSYKYGNGVWIGRTKSNSSRKGFEMIWDPNGWTGTDSNFSVKQDVVAITD
WSGYSGSFVQHPELTGLDCIRPCFWVELIRGRPRENTIWTSGSSISFCGVNSDTVN
WSWPDGAELPFTIDK

NA-A
MNPNQKIITIGSVSLTIATICFLMQIAILVTTVTLHFKQYECSSPPNNQVMLCEPTIIER
NITEIVYLTNTTIEKEICPKLAEYRNWSKPQCKITGFAPFSKDNSIRLSAGGDIWVTRE
PYVSCDPDKCYQFALGQGTTLNNRHSNDTVHDRTPYRTLLMNELGVPFHLGTKQV
CIAWSSSSCHDGKAWLHVCITGDDENATASFIYNGRLVDSIGSWSKKILRTQESEC
VCINGTCTVVMTDGSASGRADTKILFIEEGKIVHISPLSGSAQHVEECSCYPRYPGV
RCVCRDNWKGSNRPIVDINVKDYSIVSSYVCSGLVGDTPRKNDSSSSSHCLNPNN
EEGGHGVKGWAFDDGNDVWMGRTISEKLRLGYETFKVIEGWSKPNSKLQINRQVI
VERGNRSGYSGIFSVEGKSCINRCFYVELIRGRKQETEVWWTSNSIVVFCGTSGTY
GTGSWPDGADINLMPI

SEQUENCE LISTING

```
<160> NUMBER OF SEQ ID NOS: 8

<210> SEQ ID NO 1
<211> LENGTH: 566
<212> TYPE: PRT
<213> ORGANISM: Influenza A virus

<400> SEQUENCE: 1

Met Lys Ala Ile Leu Val Val Leu Leu Tyr Thr Phe Thr Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Asn Ser Asp Asn Gly Thr Cys Tyr Pro Gly Asp Phe
            100                 105                 110

Ile Asn Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Asn Gln Ser Tyr Ile Asn Asp Lys Gly Lys Glu Val Leu Val
            180                 185                 190

Leu Trp Gly Ile His His Pro Ser Thr Thr Ala Asp Gln Gln Ser Leu
        195                 200                 205

Tyr Gln Asn Ala Asp Ala Tyr Val Phe Val Gly Thr Ser Arg Tyr Ser
    210                 215                 220

Lys Lys Phe Lys Pro Glu Ile Ala Thr Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Thr Met Glu Arg Asn Ala Gly Ser Gly Ile Ile Ile Ser Asp Thr Pro
        275                 280                 285

Val His Asp Cys Asn Thr Thr Cys Gln Thr Pro Glu Gly Ala Ile Asn
    290                 295                 300

Thr Ser Leu Pro Phe Gln Asn Val His Pro Ile Thr Ile Gly Lys Cys
305                 310                 315                 320
```

-continued

```
Pro Lys Tyr Val Lys Ser Thr Lys Leu Arg Leu Ala Thr Gly Leu Arg
            325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
        370                 375                 380

Thr Gln Asn Ala Ile Asp Lys Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
        450                 455                 460

Lys Val Arg Asn Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Lys Ile Asp Gly Val Lys Leu Glu Ser Thr Arg Ile Tyr
            515                 520                 525

Gln Ile Leu Ala Ile Tyr Ser Thr Val Ala Ser Ser Leu Val Leu Val
        530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

```
<210> SEQ ID NO 2
<211> LENGTH: 562
<212> TYPE: PRT
<213> ORGANISM: Influenza A virus

<400> SEQUENCE: 2
```

```
Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
        50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
```

-continued

```
              115               120                125

Val Lys Ile Leu Pro Lys Asp Arg Trp Thr Gln His Thr Thr Thr Gly
    130               135               140

Gly Ser Arg Ala Cys Ala Val Ser Gly Lys Pro Ser Phe Phe Arg Asn
145               150               155               160

Met Val Trp Leu Thr Lys Lys Gly Ser Asn Tyr Pro Val Ala Lys Gly
              165               170               175

Ser Tyr Asn Asn Thr Ser Gly Glu Gln Met Leu Ile Ile Trp Gly Val
              180               185               190

His His Pro Asn Asp Glu Thr Glu Gln Arg Thr Leu Tyr Gln Asn Val
              195               200               205

Gly Thr Tyr Val Ser Val Gly Thr Ser Thr Leu Asn Lys Arg Ser Thr
    210               215               220

Pro Glu Ile Ala Thr Arg Pro Lys Val Asn Gly Gln Gly Gly Arg Met
225               230               235               240

Glu Phe Ser Trp Thr Leu Leu Asp Met Trp Asp Thr Ile Asn Phe Glu
              245               250               255

Ser Thr Gly Asn Leu Ile Ala Pro Glu Tyr Gly Phe Lys Ile Ser Lys
              260               265               270

Arg Gly Ser Ser Gly Ile Met Lys Thr Glu Gly Thr Leu Glu Asn Cys
              275               280               285

Glu Thr Lys Cys Gln Thr Pro Leu Gly Ala Ile Asn Thr Thr Leu Pro
    290               295               300

Phe His Asn Ile His Pro Leu Thr Ile Gly Glu Cys Pro Lys Tyr Val
305               310               315               320

Lys Ser Glu Arg Leu Val Leu Ala Thr Gly Leu Arg Asn Val Pro Gln
              325               330               335

Ile Glu Ser Arg Gly Leu Phe Gly Ala Ile Ala Gly Phe Ile Glu Gly
              340               345               350

Gly Trp Gln Gly Met Val Asp Gly Trp Tyr Gly Tyr His His Ser Asn
              355               360               365

Asp Gln Gly Ser Gly Tyr Ala Ala Asp Lys Glu Ser Thr Gln Lys Ala
    370               375               380

Ile Asp Gly Ile Thr Asn Lys Val Asn Ser Val Ile Glu Lys Met Asn
385               390               395               400

Thr Gln Phe Glu Ala Val Gly Lys Glu Phe Asn Asn Leu Glu Arg Arg
              405               410               415

Leu Glu Asn Leu Asn Lys Lys Met Glu Asp Gly Phe Leu Asp Val Trp
              420               425               430

Thr Tyr Asn Ala Glu Leu Leu Val Leu Met Glu Asn Glu Arg Thr Leu
              435               440               445

Asp Phe His Asp Ser Asn Val Lys Asn Leu Tyr Asp Lys Val Arg Met
    450               455               460

Gln Leu Arg Asp Asn Ala Lys Glu Leu Gly Asn Gly Cys Phe Glu Phe
465               470               475               480

Tyr His Lys Cys Asp Asp Glu Cys Met Asn Ser Val Lys Asn Gly Thr
              485               490               495

Tyr Asp Tyr Pro Lys Tyr Glu Glu Glu Ser Lys Leu Asn Arg Asn Glu
              500               505               510

Ile Lys Gly Val Lys Leu Ser Asn Met Gly Val Tyr Gln Ile Leu Ala
              515               520               525

Ile Tyr Ala Thr Val Ala Gly Ser Leu Ser Leu Ala Ile Met Ile Ala
    530               535               540
```

```
Gly Ile Ser Phe Trp Met Cys Ser Asn Gly Ser Leu Gln Cys Arg Ile
545                 550                 555                 560

Cys Ile

<210> SEQ ID NO 3
<211> LENGTH: 566
<212> TYPE: PRT
<213> ORGANISM: Influenza A virus

<400> SEQUENCE: 3

Met Lys Thr Ile Ile Ala Leu Ser Tyr Ile Leu Cys Leu Val Phe Ala
1               5                   10                  15

Gln Lys Ile Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Arg Ile Glu Val Thr Asn Ala Thr Glu Leu Val Gln Asn Ser Ser Ile
        50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Asn Asn Glu Ser Phe Asn Trp Thr
        130                 135                 140

Gly Val Thr Gln Asn Gly Thr Ser Ser Ala Cys Ile Arg Arg Ser Ser
145                 150                 155                 160

Ser Ser Phe Phe Ser Arg Leu Asn Trp Leu Thr His Leu Asn Tyr Thr
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
            195                 200                 205

Phe Leu Tyr Ala Gln Ser Ser Gly Arg Ile Thr Val Ser Thr Lys Arg
        210                 215                 220

Ser Gln Gln Ala Val Ile Pro Asn Ile Gly Ser Arg Pro Arg Ile Arg
225                 230                 235                 240

Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
            275                 280                 285

Pro Ile Gly Lys Cys Lys Ser Glu Cys Ile Thr Pro Asn Gly Ser Ile
        290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
            340                 345                 350
```

-continued

```
Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
        370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
        450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asn Val Tyr Arg Asp Glu Ala Leu
                500                 505                 510

Asn Asn Arg Phe Gln Ile Lys Gly Val Glu Leu Lys Ser Gly Tyr Lys
                515                 520                 525

Asp Trp Ile Leu Trp Ile Ser Phe Ala Ile Ser Cys Phe Leu Leu Cys
        530                 535                 540

Val Ala Leu Leu Gly Phe Ile Met Trp Ala Cys Gln Lys Gly Asn Ile
545                 550                 555                 560

Arg Cys Asn Ile Cys Ile
                565
```

<210> SEQ ID NO 4
<211> LENGTH: 568
<212> TYPE: PRT
<213> ORGANISM: Influenza A virus

<400> SEQUENCE: 4

```
Met Glu Lys Ile Val Leu Pro Phe Ala Val Ile Ser Leu Val Lys Ser
1                   5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asn Gly Val Lys
        50                  55                  60

Pro Leu Ile Leu Lys Asp Cys Ser Val Ala Gly Trp Leu Leu Gly Asn
65                  70                  75                  80

Pro Met Cys Asp Glu Phe Ile Arg Val Pro Glu Trp Ser Tyr Ile Val
                85                  90                  95

Glu Arg Ala Asn Pro Ala Asn Asp Leu Cys Tyr Pro Gly Asn Leu Asn
                100                 105                 110

Asp Tyr Glu Glu Leu Lys His Leu Leu Ser Arg Ile Asn His Phe Glu
                115                 120                 125

Lys Thr Leu Ile Ile Pro Lys Ser Ser Trp Pro Asn His Glu Thr Ser
        130                 135                 140

Leu Gly Val Ser Ala Ala Cys Pro Tyr Gln Gly Thr Pro Ser Phe Phe
```

-continued

```
145                150                155                160

Arg Asn Val Val Trp Leu Ile Lys Lys Asn Asp Ala Tyr Pro Thr Ile
                 165                170                175

Lys Ile Ser Tyr Asn Asn Thr Asn Arg Glu Asp Leu Leu Ile Leu Trp
                 180                185                190

Gly Ile His His Ser Asn Asn Ala Ala Glu Gln Thr Asn Leu Tyr Lys
                 195                200                205

Asn Pro Thr Thr Tyr Val Ser Val Gly Thr Ser Thr Leu Asn Gln Arg
    210                215                220

Leu Val Pro Lys Ile Ala Thr Arg Ser Gln Val Asn Gly Gln Arg Gly
225                230                235                240

Arg Met Asp Phe Phe Trp Thr Ile Leu Lys Pro Asn Asp Ala Ile His
                 245                250                255

Phe Glu Ser Asn Gly Asn Phe Ile Ala Pro Glu Tyr Ala Tyr Lys Ile
                 260                265                270

Val Lys Lys Gly Asp Ser Thr Ile Met Lys Ser Glu Val Glu Tyr Gly
                 275                280                285

His Cys Asn Thr Lys Cys Gln Thr Pro Ile Gly Ala Ile Asn Ser Ser
    290                295                300

Met Pro Phe His Asn Ile His Pro Leu Thr Ile Gly Glu Cys Pro Lys
305                310                315                320

Tyr Val Lys Ser Asn Lys Leu Val Leu Ala Thr Gly Leu Arg Asn Ser
                 325                330                335

Pro Leu Asn Val Pro Gln Arg Glu Thr Arg Gly Leu Phe Gly Ala Ile
                 340                345                350

Ala Gly Phe Ile Glu Gly Gly Trp Gln Gly Met Val Asp Gly Trp Tyr
                 355                360                365

Gly Tyr His His Ser Asn Glu Gln Gly Ser Gly Tyr Ala Ala Asp Lys
    370                375                380

Glu Ser Thr Gln Lys Ala Ile Asp Gly Ile Thr Asn Lys Val Asn Ser
385                390                395                400

Ile Ile Asp Lys Met Asn Thr Gln Phe Glu Ala Val Gly Lys Glu Phe
                 405                410                415

Asn Asn Leu Glu Arg Arg Ile Glu Asn Leu Asn Lys Lys Met Glu Asp
                 420                425                430

Gly Phe Leu Asp Val Trp Thr Tyr Asn Ala Glu Leu Leu Val Leu Met
                 435                440                445

Glu Asn Glu Arg Thr Leu Asp Phe His Asp Ser Asn Val Lys Asn Leu
    450                455                460

Tyr Asp Lys Val Arg Leu Gln Leu Arg Asp Asn Ala Lys Glu Leu Gly
465                470                475                480

Asn Gly Cys Phe Glu Phe Tyr His Lys Cys Asp Asn Glu Cys Met Glu
                 485                490                495

Ser Val Arg Asn Gly Thr Tyr Asp Tyr Pro Gln Tyr Ser Glu Glu Ala
                 500                505                510

Arg Leu Asn Arg Glu Glu Ile Ser Gly Val Lys Leu Glu Ser Met Gly
                 515                520                525

Thr Tyr Gln Ile Leu Ser Ile Tyr Ser Thr Val Ala Ser Ser Leu Ala
    530                535                540

Leu Ala Ile Met Ile Ala Gly Leu Ser Phe Trp Met Cys Ser Asn Gly
545                550                555                560

Ser Leu Gln Cys Arg Ile Cys Ile
                 565
```

```
<210> SEQ ID NO 5
<211> LENGTH: 560
<212> TYPE: PRT
<213> ORGANISM: Influenza A virus

<400> SEQUENCE: 5

Met Asn Thr Gln Ile Leu Ala Leu Val Ala Cys Met Leu Ile Gly Val
1               5                   10                  15

Lys Gly Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Thr Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ser Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Lys Pro Ala Leu Ile Ile Trp Gly Ile His
            180                 185                 190

His Ser Gly Ser Thr Thr Glu Gln Thr Lys Leu Tyr Gly Ser Gly Asn
        195                 200                 205

Lys Leu Ile Thr Val Gly Ser Ser Asn Tyr Gln Gln Ser Phe Val Pro
    210                 215                 220

Ser Pro Gly Ala Arg Pro Gln Val Asn Gly Gln Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asn Ser Arg Ala Val Gly Lys Cys Pro Arg Tyr Val Lys Gln
305                 310                 315                 320

Glu Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
```

-continued

```
                370                 375                 380
Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Met Thr Glu Val Trp Ser
                420                 425                 430

Tyr Asn Ala Glu Leu Leu Val Ala Met Glu Asn Gln His Thr Ile Asp
                435                 440                 445

Leu Ala Asp Ser Glu Met Asn Lys Leu Tyr Glu Arg Val Lys Arg Gln
                450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
                500                 505                 510

Asp Pro Val Lys Leu Ser Ser Gly Tyr Lys Asp Val Ile Leu Trp Phe
                515                 520                 525

Ser Phe Gly Ala Ser Cys Phe Ile Leu Leu Ala Ile Ala Met Gly Leu
                530                 535                 540

Val Phe Ile Cys Val Lys Asn Gly Asn Met Arg Cys Thr Ile Cys Ile
545                 550                 555                 560
```

<210> SEQ ID NO 6
<211> LENGTH: 583
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 6

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
                35                  40                  45

Thr Thr Pro Thr Lys Ser His Phe Ala Asn Leu Lys Gly Thr Lys Thr
                50                  55                  60

Arg Gly Lys Leu Cys Pro Lys Cys Leu Asn Cys Thr Asp Leu Asp Val
65                  70                  75                  80

Ala Leu Gly Arg Pro Lys Cys Met Gly Thr Ile Pro Ser Ala Lys Ala
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
                115                 120                 125

Tyr Glu Lys Ile Arg Leu Ser Thr His Asn Val Ile Asn Ala Glu Lys
                130                 135                 140

Ala Pro Gly Gly Pro Tyr Arg Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175
```

-continued

```
Asp Asn Asn Lys Thr Ala Thr Asn Pro Leu Thr Val Glu Val Pro Tyr
            180                 185                 190

Ile Cys Thr Glu Gly Glu Asp Gln Ile Thr Val Trp Gly Phe His Ser
            195                 200                 205

Asp Asn Glu Thr Gln Met Lys Lys Leu Tyr Gly Asp Ser Lys Pro Gln
            210                 215                 220

Lys Phe Thr Ser Ser Ala Asn Gly Val Thr Thr His Tyr Val Ser Gln
225                 230                 235                 240

Ile Gly Gly Phe Pro Asn Gln Thr Glu Asp Gly Gly Leu Pro Gln Ser
                245                 250                 255

Gly Arg Ile Val Val Asp Tyr Met Val Gln Lys Ser Gly Lys Thr Gly
            260                 265                 270

Thr Ile Val Tyr Gln Arg Gly Ile Leu Leu Pro Gln Lys Val Trp Cys
            275                 280                 285

Ala Ser Gly Arg Ser Lys Val Ile Lys Gly Ser Leu Pro Leu Ile Gly
            290                 295                 300

Glu Ala Asp Cys Leu His Glu Lys Tyr Gly Gly Leu Asn Lys Ser Lys
305                 310                 315                 320

Pro Tyr Tyr Thr Gly Glu His Ala Lys Ala Ile Gly Asn Cys Pro Ile
                325                 330                 335

Trp Val Lys Thr Pro Leu Lys Leu Ala Asn Gly Thr Lys Tyr Arg Pro
            340                 345                 350

Pro Ala Lys Leu Leu Lys Glu Arg Gly Phe Phe Gly Ala Ile Ala Gly
            355                 360                 365

Phe Leu Glu Gly Gly Trp Glu Gly Met Ile Ala Gly Trp His Gly Tyr
            370                 375                 380

Thr Ser His Gly Ala His Gly Val Ala Val Ala Ala Asp Leu Lys Ser
385                 390                 395                 400

Thr Gln Glu Ala Ile Asn Lys Ile Thr Lys Asn Leu Asn Ser Leu Ser
                405                 410                 415

Glu Leu Glu Val Lys Asn Leu Gln Arg Leu Ser Gly Ala Met Asp Glu
            420                 425                 430

Leu His Asn Glu Ile Leu Glu Leu Asp Glu Lys Val Asp Asp Leu Arg
            435                 440                 445

Ala Asp Thr Ile Ser Ser Gln Ile Glu Leu Ala Val Leu Leu Ser Asn
            450                 455                 460

Glu Gly Ile Ile Asn Ser Glu Asp Glu His Leu Leu Ala Leu Glu Arg
465                 470                 475                 480

Lys Leu Lys Lys Met Leu Gly Pro Ser Ala Val Asp Ile Gly Asn Gly
                485                 490                 495

Cys Phe Glu Thr Lys His Lys Cys Asn Gln Thr Cys Leu Asp Arg Ile
            500                 505                 510

Ala Ala Gly Thr Phe Asn Ala Gly Glu Phe Ser Leu Pro Thr Phe Asp
            515                 520                 525

Ser Leu Asn Ile Thr Ala Ala Ser Leu Asn Asp Asp Gly Leu Asp Asn
            530                 535                 540

His Thr Ile Leu Leu Tyr Tyr Ser Thr Ala Ala Ser Ser Leu Ala Val
545                 550                 555                 560

Thr Leu Met Ile Ala Ile Phe Ile Val Tyr Met Val Ser Arg Asp Asn
                565                 570                 575

Val Ser Cys Ser Ile Cys Leu
                580
```

-continued

```
<210> SEQ ID NO 7
<211> LENGTH: 469
<212> TYPE: PRT
<213> ORGANISM: Influenza A virus

<400> SEQUENCE: 7

Met Asn Pro Asn Gln Lys Ile Ile Thr Ile Gly Ser Ile Cys Met Ala
1               5                   10                  15

Ile Gly Ile Ile Ser Leu Ile Leu Gln Ile Gly Asn Ile Ile Ser Ile
            20                  25                  30

Trp Val Ser His Ser Ile Gln Thr Gly Ser Gln Asn His Thr Gly Ile
        35                  40                  45

Cys Asn Gln Arg Ile Ile Thr Tyr Glu Asn Ser Thr Trp Val Asn Gln
    50                  55                  60

Thr Tyr Val Asn Ile Ser Asn Thr Asn Val Val Ala Gly Lys Asp Val
65                  70                  75                  80

Thr Ser Val Thr Leu Ala Gly Asn Ser Ser Leu Cys Pro Ile Ser Gly
                85                  90                  95

Trp Ala Ile Tyr Ser Lys Asp Asn Ser Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Ala Leu Met Ser
145                 150                 155                 160

Cys Pro Ile Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
            195                 200                 205

Asn Gly Ile Ile Thr Glu Thr Ile Lys Ser Trp Arg Lys Asn Ile Leu
    210                 215                 220

Arg Thr Gln Glu Ser Glu Cys Val Cys Val Asn Gly Ser Cys Phe Thr
225                 230                 235                 240

Ile Met Thr Asp Gly Pro Ser Asp Gly Gln Ala Ser Tyr Lys Ile Phe
                245                 250                 255

Lys Ile Glu Lys Gly Lys Ile Thr Lys Ser Ile Glu Leu Asn Ala Pro
            260                 265                 270

Asn Tyr His Tyr Glu Glu Cys Ser Cys Tyr Pro Asp Thr Gly Thr Val
    275                 280                 285

Met Cys Val Cys Arg Asp Asn Trp His Gly Ser Asn Arg Pro Trp Val
    290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Thr Gly Ser Cys Gly
                325                 330                 335

Pro Val Thr Val Asp Gly Ala Asn Gly Val Lys Gly Phe Ser Tyr Lys
            340                 345                 350

Tyr Gly Asn Gly Val Trp Ile Gly Arg Thr Lys Ser Asn Ser Ser Arg
        355                 360                 365

Lys Gly Phe Glu Met Ile Trp Asp Pro Asn Gly Trp Thr Gly Thr Asp
    370                 375                 380
```

-continued

```
Ser Asn Phe Ser Val Lys Gln Asp Val Val Ala Ile Thr Asp Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Arg
                420                 425                 430

Glu Asn Thr Ile Trp Thr Ser Gly Ser Ser Ile Ser Phe Cys Gly Val
            435                 440                 445

Asn Ser Asp Thr Val Asn Trp Ser Trp Pro Asp Gly Ala Glu Leu Pro
    450                 455                 460

Phe Thr Ile Asp Lys
465

<210> SEQ ID NO 8
<211> LENGTH: 469
<212> TYPE: PRT
<213> ORGANISM: Influenza A virus

<400> SEQUENCE: 8

Met Asn Pro Asn Gln Lys Ile Ile Thr Ile Gly Ser Val Ser Leu Thr
1               5                   10                  15

Ile Ala Thr Ile Cys Phe Leu Met Gln Ile Ala Ile Leu Val Thr Thr
                20                  25                  30

Val Thr Leu His Phe Lys Gln Tyr Glu Cys Ser Ser Pro Pro Asn Asn
            35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Lys Ile Thr Gly
                85                  90                  95

Phe Ala Pro Phe Ser Lys Asp Asn Ser Ile Arg Leu Ser Ala Gly Gly
                100                 105                 110

Asp Ile Trp Val Thr Arg Glu Pro Tyr Val Ser Cys Asp Pro Asp Lys
            115                 120                 125

Cys Tyr Gln Phe Ala Leu Gly Gln Gly Thr Thr Leu Asn Asn Arg His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
                180                 185                 190

Cys Ile Thr Gly Asp Asp Glu Asn Ala Thr Ala Ser Phe Ile Tyr Asn
            195                 200                 205

Gly Arg Leu Val Asp Ser Ile Gly Ser Trp Ser Lys Lys Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Lys Ile Leu Phe
                245                 250                 255

Ile Glu Glu Gly Lys Ile Val His Ile Ser Pro Leu Ser Gly Ser Ala
                260                 265                 270

Gln His Val Glu Glu Cys Ser Cys Tyr Pro Arg Tyr Pro Gly Val Arg
    275                 280                 285
```

-continued

```
Cys Val Cys Arg Asp Asn Trp Lys Gly Ser Asn Arg Pro Ile Val Asp
    290             295             300

Ile Asn Val Lys Asp Tyr Ser Ile Val Ser Ser Tyr Val Cys Ser Gly
305             310             315             320

Leu Val Gly Asp Thr Pro Arg Lys Asn Asp Ser Ser Ser Ser Ser His
            325             330             335

Cys Leu Asn Pro Asn Asn Glu Glu Gly Gly His Gly Val Lys Gly Trp
            340             345             350

Ala Phe Asp Asp Gly Asn Asp Val Trp Met Gly Arg Thr Ile Ser Glu
            355             360             365

Lys Leu Arg Leu Gly Tyr Glu Thr Phe Lys Val Ile Glu Gly Trp Ser
    370             375             380

Lys Pro Asn Ser Lys Leu Gln Ile Asn Arg Gln Val Ile Val Glu Arg
385             390             395             400

Gly Asn Arg Ser Gly Tyr Ser Gly Ile Phe Ser Val Glu Gly Lys Ser
            405             410             415

Cys Ile Asn Arg Cys Phe Tyr Val Glu Leu Ile Arg Gly Arg Lys Gln
            420             425             430

Glu Thr Glu Val Trp Trp Thr Ser Asn Ser Ile Val Val Phe Cys Gly
            435             440             445

Thr Ser Gly Thr Tyr Gly Thr Gly Ser Trp Pro Asp Gly Ala Asp Ile
    450             455             460

Asn Leu Met Pro Ile
465
```

BROADLY REACTIVE VIRAL ANTIGENS AS IMMUNOGENS, COMPOSITIONS AND METHODS OF USE THEREOF

CROSS REFERENCE TO RELATED APPLICATION

This application is the U.S. National Stage Application, pursuant to 35 U.S.C. § 371 of PCT International Application No. PCT/US2021/012695, filed on Jan. 8, 2021 designating the United States and published in English, which claims priority to and the benefit of provisional application No. 62/959,404, filed on Jan. 10, 2020, the contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 19, 2021, is named 173093_011401PCT_SL.txt and is 37,938 bytes in size.

BACKGROUND

Influenza virus infection is an important cause of medically attended acute respiratory illness each year and imposes substantial morbidity, mortality and economic burdens both in the United States and worldwide. Shortly before the 2009 influenza pandemic, influenza-associated mortality accounted for over 611,000 years of life lost annually with an estimated cost to society of $87 billion each year. The U.S. Centers for Disease Control and Prevention estimated in 2017 that the seasonal flu vaccine was only 42% effective. This limited effectiveness was due to a mutation that occurred in the influenza A H3N2 vaccine strain that causes flu in infected individuals. In addition, cases of flu caused by influenza B viruses have risen in the time period from 2017 to 2018. Because a bad flu season can kill on the order of 50,000 people in the United States alone, new and improved immunogens and vaccines that provide broad protection against viruses, particularly, influenza virus strains in present and future circulation, are urgently required.

Infections from other virus types, such as coronaviruses, also cause serious disease and pathology in humans and in other species, for example, avian species, such as poultry. Such infections and disease adversely affect the health and performance of meat-producing and egg-producing avian animals, e.g., chickens, resulting in significant economic losses in the industry. Thus, new and improved immunogens and vaccines that provide broad protection against other virus strains, e.g., avian viruses and strains thereof, in present and future circulation, are also needed.

SUMMARY OF THE DISCLOSURE

As described herein, non-naturally occurring, broadly reactive antigens and antigen sequences derived from influenza viruses, such as influenza H1, H2, H3, H5, or H7 viruses (also referred to as "H1, H2, H3, H5 or H7 influenza," "H1, H2, H3, H5, or H7 influenza viruses," or simply, "H1, H2, H3, H5, or H7" herein) are provided. In addition, non-naturally occurring, broadly reactive antigens and antigen sequences derived from other virus types, such as avian infectious bronchitis virus (IBV), a coronavirus, are provided.

The influenza virus and IBV antigens as described herein are may be structural proteins or peptides and include, for example, the hemagglutinin (HA) protein, or the HA1 (head) or HA2 (tail or stalk) portions of the HA protein, and are potent immunogens that elicit a broadly reactive immune response against the HA protein and, ultimately, against present and future virus strains in a subject. As referred to herein, the virus antigens or antigen sequences (e.g., influenza virus or IBV antigens) that elicit an immune response in a subject are immunogenic antigens (i.e., immunogens). These influenza virus and IBV immunogens are termed broadly reactive, because they can elicit the production of broadly reactive antibodies that are directed against different subtypes or strains of influenza viruses or IBV having both sequence similarity and variability, and epitope (antigenic determinant) diversity in their protein antigens and sequences thereof, in particular, the HA or neuraminidase (NA) antigen of influenza virus, or the HA antigen of IBV.

There are four different types of influenza viruses, three of which (influenza A, B, and C) infect people. Of those three infectious viruses, the influenza A and B subsets are the most common types, and each of these subsets develops different strains or subtypes. Influenza A and B viruses routinely spread in humans and cause seasonal flu epidemics. By way of nonlimiting example, the H1N1, H2N2, and H5N1 strains are subtypes of influenza A that typically cause severe flu disease and that adapt to evade being eradicated by constantly changing their surface proteins, such as the hemagglutinin (HA) protein. Strains of influenza virus have been particularly problematic to treat because of unusually high rate of mutation and an inability to generate vaccines that were effective against the relatively rapid changes that occurred in the HA surface protein.

In an embodiment, the antigen (antigen sequence) that is immunogenic is derived from influenza A virus. In certain embodiments, the immunogen is derived from an H1, H2, H3, H5, or H7 influenza virus strain or type. In an embodiment, the immunogen is derived from influenza B virus. In an embodiment, the antigen is a structural protein of the virus. In a particular embodiment, the influenza antigen is hemagglutinin (HA). In another particular embodiment, the influenza antigen is neuraminidase (NA).

Avian infectious bronchitis virus (IBV) is a coronavirus which infects poultry, e.g., hens and chickens, causing the associated disease, infectious bronchitis (IB). It is a highly infectious avian pathogen which affects the respiratory tract, gut, kidney and reproductive systems of chickens. In hens, the viremic IBV can also infect the oviduct, causing lesions in the magnum (the egg-white gland) and in the uterus (the egg-shell gland), leading to a decline in egg production, shell-less, fragile or roughened shells eggs (uterus lesion) with watery whites (magnum lesion). Infection of chickens at puberty, during the oviduct development, can impede oviduct formation and destroy future laying capacity, resulting in "false layers". IBV may also infect other avian species.

In an aspect, the non-naturally occurring influenza virus or IBV antigen amino acid sequences and the antigens (e.g., structural antigens) comprising the sequences described herein contain broadly reactive epitopes that reflect sequence similarities and variabilities of past, present and future influenza virus or IBV antigens. Such antigen sequences and the antigens comprising the sequences are thus "non-naturally occurring, broadly reactive" antigens. The antigens are immunogenic and, when introduced into or administered to a subject, elicit broadly reactive antibodies, such as neutralizing antibodies, directed against the influenza virus, in particular, H1, H2, H3, H5, or H7 influenza virus, protein antigens, or IBV antigens, such as HA, or an antibody binding portion thereof, in the subject. In an embodiment, the elicited antibodies are also reactive against related, yet nonidentical H1, H2, H3, H5, or H7 influenza virus types, or IBV types, respectively. In an embodiment, such influenza virus or IBV antigen sequences are amino acid sequences. In an embodiment, the influenza virus or IBV antigen sequences are polynucleotide sequences, for example, polynucleotide sequences that encode the amino acid sequences of the antigens described herein. For ease of reference, a "non-naturally occurring, broadly reactive" antigen of an influenza virus or IBV described herein is referred to as a "broadly reactive antigen."

Accordingly, the broadly reactive influenza virus or IBV antigens described herein are immunogens as they elicit a broadly reactive immune response in a subject. The immune response is particularly in the form of a neutralizing antibody response, for example, neutralizing antibodies that are specifically directed against the HA antigen of the influenza virus or IBV and that neutralize the activity of the HA protein. Accordingly, also provided are immunogens and immunogenic compositions that contain the broadly reactive influenza virus or IBV antigens described herein, including immunogenic compositions, such as vaccines (e.g., polypeptide or polynucleotide products), that induce an immune response directed against the influenza virus, such as against the HA protein of the influenza virus, in a subject. For ease of reference, a "non-naturally occurring, broadly reactive, influenza virus or IBV immunogen described herein will be referred to as a "broadly reactive immunogen."

Also provided are methods of using the immunogens as described herein to induce an immune response against influenza infection, disease, and/or the symptoms thereof, or against IBV infection, in a subject. In a particular embodiment, the influenza virus antigen is the HA, HA1, or HA2 protein of influenza virus type or subtype, or a virus type related thereto, or an antibody binding portion thereof. In another particular embodiment, the virus antigen is the HA protein of IBV, an IBV subtype, or a virus type related thereto, or an antibody binding portion thereof. Methods of using the immunogens to induce an immune response in a subject are also provided.

In an aspect, the HA or NA immunogenic antigen has an amino acid sequence that is at least or equal to 85%, at least or equal to 90%, at least or equal to 91%, at least or equal to 92%, at least or equal to 93%, at least or equal to 94%, at least or equal to 95%, at least or equal to 96%, at least or equal to 97%, at least or equal to 98%, or at least or equal to 99% identical to an HA (or an HA1 (H1) or HA2 (H2)) amino acid sequence of one or more of the HA or NA proteins as set forth in FIGS. 1A-1F (SEQ ID NOs: 1-6) and FIGS. 2A (SEQ ID NO: 7) and 2B (SEQ ID NO: 8) and infra.

In an aspect, a non-naturally occurring and immunogenic influenza virus antigen, comprising an amino acid sequence that is at least 95% identical to an amino acid sequence of a hemagglutinin (HA) antigen as set forth in FIGS. 1A-1E (SEQ ID NOs: 1-5) and infra, or an antigen binding portion thereof, is provided. In an embodiment, the influenza virus antigen comprises an amino acid sequence that is at least 98% identical to an amino acid sequence of an HA antigen as set forth in FIGS. 1A-1E (SEQ ID NOs: 1-5) and infra. In an embodiment, the influenza virus antigen comprises an amino acid sequence of an HA antigen as set forth in FIGS. 1A-1E (SEQ ID NOs: 1-5) and infra. In an embodiment, the influenza virus antigen consists of an amino acid sequence of an HA antigen as set forth in FIGS. 1A-1E (SEQ ID NOs: 1-5) and infra. In an embodiment, the influenza virus is an H1, H2, H3, H5, or H7 influenza virus.

In an aspect, a non-naturally occurring and immunogenic influenza virus antigen, comprising an amino acid sequence that is at least 95% identical to an amino acid sequence of a neuraminidase (NA) antigen as set forth in FIGS. 2A (SEQ ID NO: 7) and 2B (SEQ ID NO: 8) and infra, or an antigen binding portion thereof, is provided. In an embodiment, the influenza virus antigen comprises an amino acid sequence that is at least 98% identical to an amino acid sequence of an NA antigen as set forth in FIGS. 2A (SEQ ID NO: 7) and 2B (SEQ ID NO: 8) and infra. In an embodiment, the influenza virus antigen comprises an amino acid sequence of an NA antigen, e.g., NAT (N1) or NA2 (N2), as set forth in FIGS. 2A (SEQ ID NO: 7) and 2B (SEQ ID NO: 8) and infra. In an embodiment, the influenza virus antigen consists of an amino acid sequence of an NA antigen as set forth in FIGS. 2A (SEQ ID NO: 7) and 2B (SEQ ID NO: 8) and infra. In an embodiment, the influenza virus is an H1, H2, H3, H5, or H7 influenza virus.

In an aspect, a non-naturally occurring and immunogenic avian infectious bronchitis virus (IBV) antigen, comprising an amino acid sequence that is at least 95% identical to an amino acid sequence of a hemagglutinin (HA) antigen as set forth in FIG. 1F (SEQ ID NO: 6) and infra, or an antigen binding portion thereof, is provided. In an embodiment, the IBV antigen comprises an amino acid sequence that is at least 98% identical to an amino acid sequence of an HA antigen as set forth in FIG. 1F (SEQ ID NO: 6) and infra. In an embodiment, the IBV antigen comprises an amino acid sequence of an HA antigen as set forth in FIG. 1F (SEQ ID NO: 6) and infra. In an embodiment, the IBV antigen consists of an amino acid sequence of an HA antigen as set forth in FIG. 1F (SEQ ID NO: 6) and infra.

Provided in another aspect is a virus-like particle (VLP) comprising the influenza virus immunogenic antigen or the IBV immunogenic antigen according to any one of the foregoing aspects. In an embodiment, the VLP comprises a polynucleotide encoding the influenza virus antigen. In an embodiment, the VLP comprises a polynucleotide encoding the IBV antigen. In an embodiment, the VLP comprises a polynucleotide encoding an influenza virus HA or NA antigen. In an embodiment, the influenza virus is an H1, H2, H3, H5, or H5 influenza virus. In an embodiment, the VLP comprises a polynucleotide encoding an IBV HA antigen. In an embodiment, the HA antigen comprises the amino acid sequence of any one of FIGS. 1A-1F (SEQ ID NOs: 1-6) and as provided infra. In an embodiment, the NA antigen comprises the amino acid sequence of FIG. 2A (SEQ ID NO: 7) or FIG. 2B (SEQ ID NO: 8) and as provided infra.

In another aspect is provided a non-naturally occurring immunogen capable of generating an immune response against present and future influenza virus strains; wherein the immunogen comprises an amino acid sequence that is at least 95% identical to an amino acid sequence of a hemagglutinin (HA) antigen as set forth in FIGS. 1A-1E (SEQ ID NOs: 1-5) and as provided infra, and/or wherein the immunogen comprises an amino acid sequence that is at least 95% identical to an amino acid sequence of a neuraminidase (NA) antigen as set forth in FIGS. 2A (SEQ ID NO: 7) and 2B (SEQ ID NO: 8) and as provided infra. In an embodiment, the immunogen comprises an amino acid sequence that is at least 98% identical to an amino acid sequence of a hemagglutinin (HA) antigen as set forth in FIGS. 1A-1E (SEQ ID NOs: 1-5) and as provided infra, and/or wherein the immunogen comprises an amino acid sequence that is at least 98% identical to an amino acid sequence of a neuraminidase (NA) antigen as set forth in FIG. 2A (SEQ ID NO: 7) or 2B (SEQ ID NO: 8) and as provided infra.

In another aspect is provided a non-naturally occurring immunogen capable of generating an immune response against present and future avian infectious bronchitis virus (IBV) strains; wherein the immunogen comprises an amino acid sequence that is at least 95% identical to an amino acid sequence of hemagglutinin (HA) antigen as set forth in FIG. 1F (SEQ ID NO: 6) and as provided infra. In an embodiment, the immunogen comprises an amino acid sequence that is at least 98% identical to an amino acid sequence of hemagglutinin (HA) antigen as set forth in FIG. 1F (SEQ ID NO: 6) and as provided infra.

In an embodiment of any of the above-delineated aspects herein, the virus antigen, VLP, or immunogen elicits an immune response which includes the production of neutralizing antibodies. In an embodiment, the immune response includes the production of antibodies having hemagglutinin inhibitory activity and/or neuraminidase inhibitory activity. In an embodiment, the immune response further includes the production of T-lymphocytes.

Provided in another aspect is a pharmaceutically acceptable composition comprising the influenza virus or IBV antigen, immunogen, or VLP of any of the foregoing aspects and delineated embodiments, and a pharmaceutically acceptable carrier, diluent, or excipient. In an embodiment, the composition further comprises an adjuvant. In an embodiment, the virus or virus antigen is derived from H1, H2, H3, H5, or H7 influenza virus. In an embodiment, the virus or virus antigen is derived from IBV.

Provided in another aspect is an immunogenic composition or vaccine comprising the influenza virus or IBV antigen, immunogen, or VLP of any of the foregoing aspects and delineated embodiments.

Provided in another aspect is a pharmaceutically acceptable composition comprising the immunogenic composition or vaccine of the above-delineated aspect and a pharmaceutically acceptable carrier, diluent, or excipient.

Provided in another aspect is a method of generating an immune response in a subject, in which the method comprises administering to a subject in need thereof an effective amount of the virus antigen, VLP, immunogen, immunogenic composition, vaccine, or pharmaceutical composition of any of the foregoing aspects and delineated embodiments. In an embodiment of the method, the immune response elicited comprises the production of neutralizing antibodies and/or T-lymphocytes. In an embodiment of the method, an adjuvant is concomitantly administered to the subject. In an embodiment of the method, the immune response is prophylactic or therapeutic. In an embodiment of the method, the subject is a human subject. In an embodiment of the method, the subject is a non-human subject or a veterinary subject.

Provided in another aspect is a polynucleotide encoding the virus antigen of any of the foregoing aspects and delineated embodiments. In an embodiment, the virus antigen is an HA protein antigen. In a particular embodiment, the HA protein antigen comprises an amino acid sequence of any one of FIGS. 1A-1F (SEQ ID NOs: 1-6) and as provided infra. In an embodiment, the virus antigen is an NA protein antigen. In a particular embodiment, the NA protein antigen comprises an amino acid sequence of FIG. 2A (SEQ ID NO: 7) or FIG. 2B (SEQ ID NO: 8) and as provided infra. In an embodiment, the virus is influenza virus. In an embodiment, the influenza virus is an H1, H2, H3, H5, or H7 influenza virus. In an embodiment, the virus is of avian infectious bronchitis virus (IBV). In an embodiment, the above-delineated polynucleotide is contained in a composition, which includes a pharmaceutically-acceptable carrier, diluent, or excipient. In an embodiment, the above-delineated polynucleotide is contained in a virus-like particle (VLP).

Definitions

Unless defined otherwise, all technical and scientific terms used herein have the meaning commonly understood by a person skilled in the art to which this invention pertains or relates. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics,* 5th Ed., R. Rieger et al. (eds.), Springer Verlag (1991); Benjamin Lewin, *Genes V*, published by Oxford University Press, 1994 (ISBN 0-19-854287-9); Kendrew et al. (eds.); *The Encyclopedia of Molecular Biology*, published by Blackwell Science Ltd., 1994 (ISBN 0-632-02182-9); *Molecular Biology and Biotechnology: a Comprehensive Desk Reference*, Robert A. Meyers (ed.), published by VCH Publishers, Inc., 1995 (ISBN 1-56081-569-8); and Hale & Marham, *The Harper Collins Dictionary of Biology* (1991). As used herein, the following terms have the meanings ascribed to them below, unless specified otherwise.

By "adjuvant" is meant a substance or vehicle that non-specifically enhances the immune response to an antigen. Adjuvants may include a suspension of minerals (e.g., alum, aluminum hydroxide, or phosphate) on which antigen is adsorbed; or water-in-oil emulsion in which antigen solution is emulsified in mineral oil (e.g., Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (see, e.g., U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include, without limitation, interleukin-1 (IL-2), the protein memory T-cell attractant "Regulated on Activation, Normal T Expressed and Secreted" (RANTES), granulocyte-macrophage-colony stimulating factor (GM-CSF), tumor necrosis factor-alpha (TNF-α), interferon-gamma (IFN-γ), granulocyte-colony stimulation factor (G-CSF), lymphocyte function-associated antigen 3 (LFA-3, also called CD58), cluster of differentiation antigen 72 (CD72), (a negative regulator of B cell responsiveness), peripheral membrane protein, B7-1 (B7-1, also called CD80), peripheral membrane protein, B7-2 (B7-2, also called CD86), the TNF ligand superfamily member 4 ligand (OX40L) or the type 2 transmembrane glycoprotein receptor belonging to the TNF superfamily (4-1BBL)

By "administer" is meant giving, supplying, dispensing, delivering, or applying a composition, agent, therapeutic and the like to a subject, or applying or bringing the composition and the like into contact with the subject. Administering or administration may be accomplished by any of a number of routes, such as, for example, without limitation, topical, oral, subcutaneous, intramuscular, intraperitoneal, intravenous (IV), (injection), intrathecal, intramuscular, dermal, intradermal, intracranial, inhalation, rectal, intravaginal, or intraocular.

By "agent" is meant any small molecule, small molecule chemical compound, antibody, nucleic acid molecule, peptide, polypeptide, or fragments thereof.

By "alteration" is meant a change (increase or decrease) in the expression levels or activity of a gene or polypeptide as detected by standard art known methods such as those described herein. As used herein, an alteration includes a 5% change in expression levels, a 10% change in expression levels, preferably a 25% change, more preferably a 40% change, and most preferably a 50% or greater change in expression levels."

By "ameliorate" is meant decrease, reduce, diminish, suppress, attenuate, arrest, or stabilize the development or progression of a disease or pathological condition.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "antibody" is meant an immunoglobulin (Ig) molecule produced by B lymphoid cells and having a specific amino acid sequence. Antibodies are evoked or elicited in subjects (humans or other animals or mammals) following exposure to a specific antigen (immunogen). A subject capable of generating antibodies/immunoglobulin (i.e., an immune response) directed against a specific antigen/immunogen is said to be immunocompetent. Antibodies are characterized by reacting specifically with (e.g., binding to) an antigen or immunogen in some demonstrable way, antibody and antigen/immunogen each being defined in terms of the other.

"Eliciting an antibody response" refers to the ability of an antigen, immunogen or other molecule to induce the production of antibodies. Antibodies are of different classes, e.g., IgM, IgG, IgA, IgE, IgD and subtypes or subclasses, e.g., IgG1, IgG2, IgG2a, IgG2b, IgG3, IgG4. An antibody/immunoglobulin response elicited in a subject can neutralize a pathogenic (e.g., infectious or disease-causing) agent by binding to epitopes (antigenic determinants) on the agent and blocking or inhibiting the activity of the agent, and/or by forming a binding complex with the agent that is cleared from the system (or body) of the subject, e.g., via the liver.

As used herein, "broadly reactive" means that an immune response is elicited against a pathogen-derived antigen protein (e.g., a virus protein sequence, such as HA or NA) in a subject that is sufficient to block, inhibit, impede, neutralize, or prevent infection of a broad range of related pathogens (such as most or all influenza viruses or IBV within a specific subtype). In an embodiment, the subject is a mammalian subject. In an embodiment, the subject is an avian subject.

By "antigen" is meant a compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In some embodiments of the disclosed compositions and methods, the antigen is an influenza hemagglutinin (HA) protein. In some embodiments of the disclosed compositions and methods, the antigen is an IBV hemagglutinin (HA) protein. In some embodiments of the disclosed compositions and methods, the antigen is a neuraminidase (NA) protein, e.g., an influenza virus NA protein. In many cases, an antigen that elicits or stimulates an immune response in a subject is termed an "immunogen."

The term "antigenic drift" refers to a mechanism for variation in organisms or microorganisms such as viruses that involves the accumulation of mutations within the genes that code for antibody-binding sites (also called antigenic determinants or epitopes). This process results in a new strain of virus/virus particles that is not inhibited or blocked as effectively by antibodies that were originally generated against the antigens of virus strains prior to mutation, thus allowing the virus to spread more easily throughout a partially immune population. By way of example, antigenic drift occurs in both influenza A and influenza B viruses.

In the context of a live virus, the term "attenuated" reflects a virus that is attenuated if its ability to infect a cell or subject and/or its ability to produce disease is reduced (for example, diminished, abrogated, or eliminated) compared to the ability of a wild-type virus to produce disease in the subject. Typically, an attenuated virus retains at least some capacity to elicit an immune response following administration to an immunocompetent subject. In some cases, an attenuated virus can elicit a protective immune response without causing any signs or symptoms of infection. In some embodiments, the ability of an attenuated virus to cause disease or pathology in a subject is reduced at least about or equal to 5%, or at least about or equal to 10%, or at least about or equal to 25%, at least about or equal to 50%, at least about or equal to 75%, or at least about or equal to 80%, or at least about or equal to 85%, or at least about or equal to 90%, or at least about or equal to 95%, or greater, relative to the ability of a wild-type virus to cause disease or pathology in the subject.

The term "clade" refers to the different categorizations (often called subtypes) of the known influenza viruses, such as, e.g., the influenza A H3N2 virus. By way of example, viruses in an H3N2 clade are genetically related, but do not share the exact viral genome. As appreciated by the skilled practitioner, there are many clades and subclades of H3N2 virus subtypes designated in the art. By way of example, one clade is 3C.2a; subclades of this clade include 3C.2a.1, 3C.2a.2, 3C.2a.3 and 3C.2a.4. In addition, there are at least ten different clades of H5N1 virus subtypes designated in the art: clade 0 clade 1, clade 2, clade 3, clade 4, clade 5, clade 6, clade 7, clade 8 and clade 9 (Abdel-Ghafar et al., *N Engl J Med* 358:261-273, 2008). Clade 2 is further divided into sub-clades (including clade 2.1, clade 2.2, clade 2.3, clade 2.4 and clade 2.5).

A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells. Codon optimization does not alter the amino acid sequence of the encoded protein.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of an analyte, compound, agent, or substance to be detected. By "detectable label" is meant a composition that, when linked to a molecule of interest, renders the latter detectable, e.g., via spectroscopic, photochemical, biochemical, immunochemical, or chemical means. Nonlimiting examples of useful detectable labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition, disorder, or pathology that damages or interferes with the normal function of a cell, tissue, or organ. Examples of diseases include those caused by influenza virus infection and the symptoms and adverse effects that are caused by infection of the body with the H1, H2, H3, H5, or H7 influenza virus. Influenza virus causes flu and its symptoms in infected individuals. Examples of diseases include those caused by avian infectious bronchitis virus infection and the symptoms and adverse effects that are caused by infection of the body with IBV.

By "effective amount" is meant the amount of an active therapeutic agent, composition, compound, biologic (e.g., a vaccine or therapeutic peptide, polypeptide, or polynucleotide) required to ameliorate, reduce, improve, abrogate, diminish, or eliminate the symptoms and/or effects of a disease, condition, or pathology relative to an untreated patient. In one embodiment, an effective amount is the amount of an antigen required to elicit an immune response. The effective amount of an immunogen or a composition comprising the immunogen, as used to practice the methods of therapeutic treatment of a disease, condition, or pathology, varies depending upon the manner of administration, the age, body weight, and general health of the subject. Ultimately, the attending physician or veterinarian will decide the appropriate amount and dosage regimen. Such amount is referred to as an "effective" amount.

A "therapeutically effective amount" refers to a quantity of a specified agent sufficient to achieve a desired effect in a subject being treated with that agent. For example, this may be the amount of an influenza virus immunogen or vaccine useful for eliciting an immune response in a subject and/or for preventing infection by influenza virus. Ideally, in the context of the present disclosure, a therapeutically effective amount of an influenza vaccine or immunogenic composition or of an IBV vaccine or immunogenic composition is an amount sufficient to increase resistance to, prevent, ameliorate, reduce, and/or treat infection caused by influenza virus in a subject without causing a substantial cytotoxic effect in the subject. The effective amount of an immunogenic composition (or vaccine) useful for increasing resistance to, preventing, ameliorating, reducing, and/or treating infection in a subject depends on, for example, the subject being treated, the manner of administration of the therapeutic composition and other factors, as noted supra.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids. A portion or fragment of a polypeptide may be a peptide. In the case of an antibody or immunoglobulin fragment, the fragment typically binds to the target antigen.

By "fusion protein" is meant a protein generated by expression of a nucleic acid (polynucleotide) sequence engineered from nucleic acid sequences encoding at least a portion of two different (heterologous) proteins or peptides. To create a fusion protein, the nucleic acid sequences must be in the same reading frame and contain no internal stop codons. For example, a fusion protein includes an influenza HA protein or NA protein fused to a heterologous protein.

By "genetic vaccine" is meant an immunogenic composition comprising a polynucleotide encoding an antigen."

By "virus polypeptide," such as an H1, H2, H3, H5, H7 influenza virus, or an IBV polypeptide is meant an amino acid sequence that is at least 85% identical, or at least 95% or greater identical, to an amino acid sequence of an antigen, e.g., an HA or NA antigen, as set forth in FIGS. 1A-1F (SEQ ID NOs: 1-6) and FIGS. 2A (SEQ ID NO: 7) and 2B (SEQ ID NO: 8) and infra, or a fragment thereof capable of inducing an immune response against the virus, virus infection, and/or the symptoms thereof in an immunized subject. In embodiments, an influenza virus or IBV polypeptide comprises or consists of the amino acid sequences or a fragment thereof as described herein and shown in FIGS. TA-1F (SEQ ID NOs: 1-6) and FIGS. 2A (SEQ ID NO: 7) and 2B (SEQ ID NO: 8) and infra.

By "virus polynucleotide" is meant a nucleic acid molecule encoding an influenza virus polypeptide, such as an H1, H2, H3, H5, H7 influenza virus, or an IBV polypeptide (antigen or antigen protein), as described herein.

The term "Hemagglutinin (HA)" refers to a surface glycoprotein expressed by an influenza virus or by IBV. HA mediates binding of the virus particle to a host cell and subsequent entry of the virus into the host cell. The nucleotide and amino acid sequences of numerous influenza HA proteins are known in the art and are publicly available, such as those deposited in the publicly accessible GenBank (NCBI) and UniProtKB databases. By way of nonlimiting example, a list of GenBank Accession Nos. of H5N1 HA sequences may be found in US Patent Application Publication US 2015/0030628. A nonlimiting example of the amino acid sequence of the HA protein of influenza A virus (strain A/Puerto Rico/8/1934 H1N1) is provided under UniProtKB Accession No. P03452 (HEMA_134A1). A nonlimiting example of the amino acid sequence of the HA protein of an influenza A, H3N2 virus, (A/Hong Kong/1-4/1968(H3N2), is provided under Accession Number CY033017. HA (along with neuraminidase (NA)) is one of the two major influenza virus antigenic proteins having antigenic determinants (epitopes) that are recognized and bound by antibodies/immunoglobulins. In embodiments, HA is HA1 (H1) or HA2 (H2).

In embodiments, an HA protein or fragment thereof may have at least about or equal to 85%, or at least about or equal to 90%, 95%, 98%, 99%, or greater, amino acid sequence identity to the amino acid sequence of a representative influenza A virus HA protein or a fragment thereof.

In an embodiment, the HA immunogenic antigen is an H1 HA protein, which comprises or consists of the following amino acid sequence:

Y3
(SEQ ID NO: 1)
MKAILVVLLYTFTTANADTLCIGYHANNSTDTVDTVLEKNVTVTHSV

NLLEDKHNGKLCKLRGVAPLHLGKCNIAGWILGNPECESLSTASSWS

YIVETSNSDNGTCYPGDFINYEELREQLSSVSSFERFEIFPKTSSWP

NHDSNKGVTAACPHAGAKSFYKNLIWLVKKGNSYPKLNQSYINDKGK

EVLVLWGIHHPSTTADQQSLYQNADAYVFVGTSRYSKKFKPEIATRP

-continued

KVRDQEGRMNYYWTLVEPGDKITFEATGNLVVPRYAFTMERNAGSGI

IISDTPVHDCNTTCQTPEGAINTSLPFQNVHPITIGKCPKYVKSTKL

RLATGLRNVPSIQSRGLFGAIAGFIEGGWTGMVDGWYGYHHQNEQGS

GYAADLKSTQNAIDKITNKVNSVIEKMNTQFTAVGKEFNHLEKRIEN

LNKKVDDGFLDIWTYNAELLVLLENERTLDYHDSNVKNLYEKVRNQL

KNNAKEIGNGCFEFYHKCDNTCMESVKNGTYDYPKYSEEAKLNREKI

DGVKLESTRIYQILAIYSTVASSLVLWSLGAISFWMCSNGSLQCRICI.

In an embodiment, the HA immunogenic antigen is an H2 HA protein, which comprises or consists of the following amino acid sequence:

Z10

(SEQ ID NO: 2)

MAIIYLILLLFTAVRGDQICIGYHANNSTEKVDTILERNVTVTHAKDIL

EKTHNGKLCKLNGIPPLELGDCSIAGWLLGNPECDRLLSVPEWSYIME

KENPRDGLCYPGSFNDYEELKHLLSSVKHFEKVKILPKDRWTQHTTTG

GSRACAVSGKPSFFRNMVWLTKKGSNYPVAKGSYNNTSGEQMLIIWGV

HHPNDETEQRTLYQNVGTYVSVGTSTLNKRSTPEIATRPKVNGQGGRM

EFSWTLLDMWDTINFESTGNLIAPEYGFKISKRGSSGIMKTEGTLENC

ETKCQTPLGAINTTLPFHNIHPLTIGECPKYVKSERLVLATGLRNVPQ

IESRGLFGAIAGFIEGGWQGMVDGWYGYHHSNDQGSGYAADKESTQKA

IDGITNKVNSVIEKMNTQFEAVGKEFNNLERRLENLNKKMEDGFLDVW

TYNAELLVLMENERTLDEHDSNVKNLYDKVRMQLRDNAKELGNGCFEE

YHKCDDECMNSVKNGTYDYPKYEEESKLNRNEIKGVKLSNMGVYQILA

IYATVAGSLSLAIMIAGISFWMCSNGSLQCRICI.

In an embodiment, the HA immunogenic antigen is an H3 HA protein, which comprises or consists of the following amino acid sequence:

J3

(SEQ ID NO: 3)

MKTIIALSYILCLVFAQKIPGNDNSTATLCLGHHAVPNGTIVKTITNDR

IEVTNATELVQNSSIGEICDSPHQILDGENCTLIDALLGDPQCDGFQNK

KWDLFVERSKAYSNCYPYDVPDYASLRSLVASSGTLEFNNESFNWTGVT

QNGTSSACIRRSSSSFFSRLNWLTHLNYTYPALNVTMPNNEQFDKLYIW

GVHHPGTDKDQIFLYAQSSGRITVSTKRSQQAVIPNIGSRPRIRDIPSR

ISIYWTIVKPGDILLINSTGNLIAPRGYFKIRSGKSSIMRSDAPIGKCK

SECITPNGSIPNDKPFQNVNRITYGACPRYVKQSTLKLATGMRNVPEKQ

TRGIFGAIAGFIENGWEGMVDGWYGFRHQNSEGRGQAADLKSTQAAIDQ

INGKLNRLIGKTNEKFHQIEKEFSEVEGRIQDLEKYVEDTKIDLWSYNA

ELLVALENQHTIDLTDSEMNKLFEKTKKQLRENAEDMGNGCFKIYHKCD

NACIGSIRNGTYDHNVYRDEALNNRFQIKGVELKSGYKDWILWISFAIS

CFLLCVALLGFIMWACQKGNIRCNICI.

In an embodiment, the HA immunogenic antigen is an H5 HA protein, which comprises or consists of the following amino acid sequence:

IAN3

(SEQ ID NO: 4)

MEKIVLPFAVISLVKSDQICIGYHANNSTEQVDTIMEKNVTVTHAQDIL

EKTHNGKLCDLNGVKPLILKDCSVAGWLLGNPMCDEFIRVPEWSYIVER

ANPANDLCYPGNLNDYEELKHLLSRINHFEKTLIIPKSSWPNHETSLGV

SAACPYQGTPSFFRNVVWLIKKNDAYPTIKISYNNTNREDLLILWGIHH

SNNAAEQTNLYKNPTTYVSVGTSTLNQRLVPKIATRSQVNGQRGRMDFF

WTILKPNDAIHFESNGNFIAPEYAYKIVKKGDSTIMKSEVEYGHCNTKC

QTPIGAINSSMPFHNIHPLTIGECPKYVKSNKLVLATGLRNSPLNVPQR

ETRGLFGAIAGFIEGGWQGMVDGWYGYHHSNEQGSGYAADKESTQKAID

GITNKVNSIIDKMNTQFEAVGKEFNNLERRIENLNKKMEDGFLDVWTYN

AELLVLMENERTLDFHDSNVKNLYDKVRLQLRDNAKELGNGCFEFYHKC

DNECMESVRNGTYDYPQYSEEARLNREEISGVKLESMGTYQILSIYSTV

ASSLALAIMIAGLSFWMCSNGSLQCRICI.

In an embodiment, the HA immunogenic antigen is an H7 HA protein, which comprises or consists of the following amino acid sequence:

Q6

(SEQ ID NO: 5)

MNTQILALVACMLIGVKGDKICLGHHAVSNGTKVNTLTERGVEVVNATE

TVERTNIPRICSKGKRTVDLGQCGLLGTITGPPQCDQFLEFSADLIIER

REGTDVCYPGKFVNEEALRQILRESGGIDKESMGFTYSGIRTNGATSAC

RRSGSSFYAEMKWLLSNTDNAAFPQMTKSYKNTRKKPALIIWGIHHSGS

TTEQTKLYGSGNKLITVGSSNYQQSFVPSPGARPQVNGQSGRIDFHWLM

LNPNDTVTFSFNGAFIAPDRASFLRGKSMGIQSGVQVDANCEGDCYHSG

GTIISNLPFQNINSRAVGKCPRYVKQESLLLATGMKNVPEIPKGRGLFG

AIAGFIENGWEGLIDGWYGFRHQNAQGEGTAADYKSTQSAIDQITGKLN

RLIEKTNQQFELIDNEFNEVEKQIGNVINWTRDSMTEVWSYNAELLVAM

ENQHTIDLADSEMNKLYERVKRQLRENAEEDGTGCFEIFHKCDDDCMAS

IRNNTYDHSKYREEAMQNRIQIDPVKLSSGYKDVILWFSFGASCFILLA

IAMGLVFICVKNGNMRCTICI.

In an embodiment, the immunogenic antigen is a non-naturally occurring and immunogenic avian infectious bronchitis virus (IBV) protein antigen. In an embodiment, the IBV immunogenic protein antigen comprises or consists of the following amino acid sequence:

B14

(SEQ ID NO: 6)

MKAIIVLLMVVTSNADRICTGITSSNSPHVVKTATQGEVNVTGVIPLT

TTPTKSHFANLKGTKTRGKLCPKCLNCTDLDVALGRPKCMGTIPSAKA

SILHEVRPVTSGCFPIMHDRTKIRQLPNLLRGYEKIRLSTHNVINAEK

APGGPYRIGTSGSCPNITNGNGFFATMAWAVPDNNKTATNPLTVEVPY

ICTEGEDQITVWGFHSDNETQMKKLYGDSKPQKFTSSANGVTTHYVSQ

IGGFPNQTEDGGLPOSGRIVVDYMVQKSGKTGTIVYQRGILLPQKVWC

ASGRSKVIKGSLPLIGEADCLHEKYGGLNKSKPYYTGEHAKAIGNCPI 13
14

-continued

```
WVKTPLKLANGTKYRPPAKLLKERGFFGAIAGFLEGGWEGMIAGWHGY

TSHGAHGVAVAADLKSTQEAINKITKNLNSLSELEVKNLQRLSGAMDE

LHNEILELDEKVDDLRADTISSQIELAVLLSNEGIINSEDEHLLALER

KLKKMLGPSAVDIGNGCFETKHKCNQTCLDRIAAGTFNAGEFSLPTFD

SLNITAASLNDDGLDNHTILLYYSTAASSLAVTLMIAIFIVYMVSRDN

VSCSIGL.
```

"Hybridization" means hydrogen bonding, which may be Watson-Crick, Hoogsteen, or reversed Hoogsteen hydrogen bonding, between complementary nucleobases. For example, in DNA, adenine and thymine, and cytosine and guanine, are, respectively, complementary nucleobases that pair through the formation of hydrogen bonds.

The term "immune response" is meant any response mediated by an immunoresponsive cell. In one example of an immune response, leukocytes are recruited to carry out a variety of different specific functions in response to exposure to an antigen (e.g., a foreign entity). Immune responses are multifactorial processes that differ depending on the types of cells involved. Immune responses include cell-mediated responses (e.g., T cell responses), humoral responses (B cell/antibody responses), innate responses and combinations thereof.

By "immunogen" is meant a compound, composition, or substance which, under appropriate conditions, can elicit or stimulate an immune response, such as the production of antibodies, and/or a T-cell response, in an animal, including compositions that are injected into or otherwise delivered to an animal. As used herein, an "immunogenic composition" is a composition comprising an immunogen (such as an HA or NA polypeptide or a polynucleotide encoding such immunogen) or a vaccine comprising an HA or NA polypeptide or a polynucleotide encoding such immunogen). As will be appreciated by the skilled person in the art, if administered to a subject in need prior to the subject's contracting disease or experiencing full-blown disease, an immunogenic composition can be prophylactic and result in the subject's eliciting an immune response, e.g., a neutralizing antibody and/or cellular immune response, to protect against disease, or to prevent more severe disease or condition, and/or the symptoms thereof. If administered to a subject in need following the subject's contracting disease, an immunogenic composition can be therapeutic and result in the subject's eliciting an immune response, e.g., a neutralizing antibody and/or cellular immune response, to treat the disease, e.g., by reducing, diminishing, abrogating, ameliorating, abating, alleviating, or eliminating the disease, and/or the symptoms thereof. In an embodiment, the immune response is a B cell response, which results in the production of antibodies, e.g., neutralizing antibodies, directed against the immunogen or immunogenic composition comprising the antigen or antigen sequence. In a manner similar to the foregoing, in some embodiments, an immunogenic composition or vaccine can be prophylactic. In some embodiments, an immunogenic composition or vaccine can be therapeutic. In an embodiment, the disease is influenza (flu). In an embodiment, the disease is infectious bronchitis.

By "immunogenic composition" is meant a composition comprising an antigen, antigen sequence, or immunogen, wherein the composition elicits an immune response in an immunized subject.

The term "immunize" (or immunization) refers to rendering a subject protected from, or immunologically responsive to, a disease or pathology caused by a pathogenic agent, e.g., an infectious disease caused by a virus, e.g., influenza virus H1, H2, H3, H5, or H7, or IBV, such as by vaccination.

The term "Influenza virus" refers to a segmented negative-strand RNA virus that belongs to the Orthomyxoviridae family of viruses. There are three types of Influenza viruses: A, B and C. Influenza A viruses infect a wide variety of birds and mammals, including humans, horses, marine mammals, pigs, ferrets, and chickens. In animals, most influenza A viruses cause mild localized infections of the respiratory and intestinal tract. However, highly pathogenic influenza A strains, such as, without limitation, H5N1, H5N2, H5N6, H5N8, H7N9, H9N2, H1N1, H1N2, H2N1, H2N2, H2N3, H7N3, H7N7, H3N2, H3N1, and related viruses, as well as IBV, cause systemic infections in poultry in which mortality may reach 100%. H5N1 is also referred to as "avian influenza."

By "inhibitory nucleic acid" is meant a double-stranded RNA, siRNA, shRNA, or antisense RNA, or a portion thereof, or a mimetic thereof, that when administered to a mammalian cell results in a decrease (e.g., by 5%, 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid, protein, or peptide is purified if it is substantially free of cellular material, debris, non-relevant viral material, or culture medium when produced by recombinant DNA techniques, or of chemical precursors or other chemicals when chemically synthesized. Purity and homogeneity are typically determined using standard purification methods and analytical chemistry techniques, for example, polyacrylamide gel electrophoresis or high-performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified. The term "isolated" also embraces recombinant nucleic acids, proteins or viruses, as well as chemically synthesized nucleic acids or peptides.

By "isolated polynucleotide" is meant a nucleic acid (e.g., a DNA molecule) that is free of the genes which flank the gene in the naturally-occurring genome of the organism from which the nucleic acid molecule of the invention is derived. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonu- 15                                                    16 cleave digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide, such as described herein, that has been separated from components that naturally accompany it. Typically, the polypeptide is isolated when it is at least 30% by weight, at least 40%, by weight, at least 50%, by weight, at least 60%, by weight, free from the proteins and naturally-occurring organic molecules with which it is naturally associated. Preferably, an isolated polypeptide preparation is at least 75%, at least 90%, or at least 99%, by weight, free from the proteins and naturally-occurring organic molecules with which it is naturally associated. An isolated polypeptide may be obtained, for example, by extraction from a natural source; by expression of a recombinant nucleic acid encoding such a polypeptide; or by chemically synthesizing the protein. Purity can be measured by any standard, appropriate method, for example, column chromatography, polyacrylamide gel electrophoresis, or by HPLC analysis. An isolated polypeptide can refer to broadly active virus immunogen polypeptide generated by the methods described herein.

By "linker" is meant one or more amino acids that serve as a spacer between two polypeptides or peptides of a fusion protein.

By "marker" is meant any protein or polynucleotide having an alteration (e.g., increase or decrease) in expression level or activity that is associated with a disease, condition, pathology, or disorder.

A "Matrix (M1) protein" refers to an influenza virus structural protein found within the viral envelope. M1 is thought to function in assembly and budding of virus following infection of a cell.

The term "Neuraminidase (NA)" refers to an influenza virus membrane glycoprotein. NA is involved in the destruction of the cellular receptor for the viral HA by cleaving terminal sialic acid residues from carbohydrate moieties on the surfaces of infected cells. NA also cleaves sialic acid residues from viral proteins, preventing aggregation of viruses. NA (along with HA) is one of the two major influenza virus antigenic determinants. In embodiments, the influenza virus NA antigen is an NAT (N1) or NA2 (N2) protein.

In an embodiment, the NA immunogenic antigen is an N1 protein, which comprises or consists of the following amino acid sequence:

NA-D
                                                    (SEQ ID NO: 7)
MNPNQKIITIGSICMAIGIISLILQIGNIISIWVSHSIQTGSQNHTGI

CNQRIITYENSTWVNQTYVNISNTNVVAGKDVTSVTLAGNSSLCPISG

WAIYSKDNSIRIGSKGDVFVIREPFISCSHLECRTFFLTQGALLNDKH

SNGTVKDRSPYRALMSCPIGEAPSPYNSRFESVAWSASACHDGMGWLT

IGISGPDNGAVAVLKYNGIITETIKSWRKNILRTQESECVCVNGSCFT

IMTDGPSDGQASYKIFKIEKGKITKSIELNAPNYHYEECSCYPDTGTV

MCVCRDNWHGSNRPWVSFNQNLDYQIGYICSGVEGDNPRPKDGTGSCG

PVTVDGANGVKGFSYKYGNGVWIGRTKSNSSRKGFEMIWDPNGWTGTD

-continued
SNFSVKQDVVAITDWSGYSGSFVQHPELTGLDCIRPCFWVELIRGRPR

ENTIWTSGSSISFCGVNSDTVNWSWPDGAELPFTIDK.

In an embodiment, the NA immunogenic antigen is an N2 protein, which comprises or consists of the following amino acid sequence:

NA-A
                                                    (SEQ ID NO: 8)
MNPNQKIITIGSVSLTIATICFLMQIAILVTTVTLHFKQYECSSPPNN

QVMLCEPTIIERNITEIVYLTNTTIEKEICPKLAEYRNWSKPQCKITG

FAPFSKDNSIRLSAGGDIWVTREPYVSCDPDKCYQFALGQGTTLNNRH

SNDTVHDRTPYRTLLMNELGVPFHLGTKQVCIAWSSSSCHDGKAWLHV

CITGDDENATASFIYNGRLVDSIGSWSKKILRTQESECVCINGTCTWM

TDGSASGRADTKILFIEEGKIVHISPLSGSAQHVEECSCYPRYPGVRC

VCRDNWKGSNRPIVDINVKDYSIVSSYVCSGLVGDTPRKNDSSSSSHC

LNPNNEEGGHGVKGWAFDDGNDVWMGRTISEKLRLGYETFKVIEGWSK

PNSKLQINRQVIVERGNRSGYSGIFSVEGKSCINRCFYVELIRGRKQE

TEVWWTSNSIVVFCGTSGTYGTGSWPDGADINLMPI.

As used herein, "obtaining" as in "obtaining an agent" includes synthesizing, isolating, purifying, purchasing, or otherwise acquiring the agent.

The term "operably linked" refers to nucleic acid sequences as used herein. By way of example, a first nucleic acid sequence is operably linked to a second nucleic acid sequence when the first nucleic acid sequence is placed in a functional relationship with the second nucleic acid sequence. For instance, a promoter is operably linked to a coding sequence if the promoter affects (allows) the transcription or expression of the coding sequence. Generally, operably linked DNA sequences are contiguous and, where necessary to join two protein-coding regions, are in the same reading frame.

The nucleotide sequence encoding an HA or NA protein that is broadly reactive (such that an immune response (e.g., an antibody response) is generated against it as well as other, perhaps antigenically drifted, yet related viruses) can be optimized for expression in mammalian cells via codon-optimization and RNA optimization (such as to increase RNA stability) using procedures and techniques practiced in the art.

A broadly reactive, immunogenic antigen, such as influenza (e.g., H1, H2, H3, H5, or H7 influenza virus), or IBV, hemagglutinin (HA) protein, for eliciting an immune response in a subject possesses a collective set of strongly immunogenic epitopes (also called antigenic determinants). An influenza or IBV virus HA protein described herein is suitable for use as an immune response-eliciting immunogen, or vaccine, which elicits a broadly reactive immune response, e.g., a neutralizing antibody response, against other related, but nonidentical, virus types which express HA proteins on the viral surface, when introduced into a host subject, in particular, a human subject infected with influenza H1, H2, H3, H5, or H7 virus, or with IBV. The immunogenic antigen (or vaccine) is advantageous for providing an anti-virus immunogen (or a vaccine) that elicits a broadly active immune response against other H1, H2, H3, H5, or H7 influenza virus HA antigens, or against other IBV HA antigens, with antigenic variability and similarity, and treats or protects against infection and disease caused by more than one H1, H2, H3, H5, or H7 influenza virus subtype, or by more than one IBV subtype.

Similarly, a broadly reactive influenza neuraminidase (NA) protein such as described herein provides an influenza NA antigen that possesses a collective set of strongly immunogenic epitopes (antigenic determinants) and is suitable for use as an immunogen, such as a vaccine or VLPs, which elicits a broadly reactive immune response, e.g., a neutralizing antibody response, against a plurality of virus types (e.g., influenza virus types) which express NA proteins on the viral surface. The immunogenic NA antigen (or vaccine) is advantageous for treating or protecting against infection and disease caused by different influenza virus types and subtypes By "open reading frame (ORF)" is meant a series of nucleotide triplets (codons) that code for amino acids without any termination codons. These sequences are usually translatable into a peptide or polypeptide.

The term "pharmaceutically acceptable vehicle" refers to conventional carriers (vehicles) and excipients that are physiologically and pharmaceutically acceptable for use, particularly in mammalian, e.g., human, subjects, as well as in other animal or avian subjects. Such pharmaceutically acceptable vehicles are known to the skilled practitioner in the pertinent art and can be readily found in *Remington's Pharmaceutical Sciences*, by E. W. Martin, Mack Publishing Co., Easton, Pa., 15th Edition (1975) and its updated editions, which describes compositions and formulations suitable for pharmaceutical delivery of one or more therapeutic compositions, such as one or more influenza or IBV immunogens (vaccines), and additional pharmaceutical agents. In general, the nature of a pharmaceutically acceptable carrier depends on the particular mode of administration being employed. For instance, parenteral formulations usually comprise injectable fluids/liquids that include pharmaceutically and physiologically acceptable fluids such as water, physiological saline, balanced salt solutions, aqueous dextrose, glycerol or the like as a vehicle or diluent. For solid compositions (for example, powder, pill, tablet, or capsule forms), conventional non-toxic solid carriers may include, for example, pharmaceutical grades of mannitol, lactose, starch, or magnesium stearate, which typically stabilize and/or increase the half-life of a composition or drug. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

By "plasmid" (or "vector") is meant a circular nucleic acid molecule capable of autonomous replication in a host cell.

By "polypeptide" (or protein) is meant a polymer in which the monomers comprise amino acid residues that are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" also refers to an amino acid that is incorporated into a protein, polypeptide, or peptide.

Conservative amino acid substitutions are those substitutions that, when made, least interfere with the properties of the original protein, that is, the structure and especially the function of the protein is conserved and is not significantly changed by such substitutions. Examples of conservative amino acid substitutions are known in the art, e.g., as set forth in, for example, U.S. Publication No. 2015/0030628. Conservative substitutions generally maintain (a) the structure of the polypeptide backbone in the area of the substitution, for example, as a sheet or helical conformation; (b) the charge or hydrophobicity of the molecule at the target site; and/or (c) the bulk of the side chain The substitutions that are generally expected to produce the greatest changes in protein properties are non-conservative, for instance, changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

By "promoter" is meant an array of nucleic acid control sequences, which direct transcription of a nucleic acid. A promoter includes necessary nucleic acid sequences near the start site of transcription. A promoter also optionally includes distal enhancer or repressor sequence elements. A "constitutive promoter" is a promoter that is continuously active and is not subject to regulation by external signals or molecules. In contrast, the activity of an "inducible promoter" is regulated by an external signal or molecule (for example, a transcription factor). By way of example, a promoter may be a CMV promoter.

As will be appreciated by the skilled practitioner in the art, the term "purified" does not require absolute purity; rather, it is intended as a relative term. Thus, for example, a purified peptide, protein, virus, polynucleotide, or other active compound is one that is isolated in whole or in part from naturally associated proteins and other contaminants. In certain embodiments, the term "substantially purified" refers to a peptide, protein, virus, polynucleotide, or other active compound that has been isolated from a cell, cell culture medium, or other crude preparation and subjected to routine methods, such as, without limitation, fractionation, chromatography, or electrophoresis, to remove various components of the initial preparation, such as proteins, cellular debris, and other components.

A "recombinant" nucleic acid, protein or virus is one that has a sequence that is not naturally occurring or that has a sequence that is made by an artificial combination of two otherwise separated segments of sequence. Such an artificial combination is often accomplished by chemical synthesis or by the artificial manipulation of isolated segments of nucleic acids, for example, by genetic engineering techniques. A "non-naturally occurring" nucleic acid, protein or virus is one that may be made via recombinant technology, artificial manipulation, genetic or molecular biological engineering, or molecular synthesis procedures and techniques, such as those commonly practiced in the art.

By "reduces" is meant a negative alteration (e.g., decrease or reduction) of at least 5%, 10%, 25%, 30%, 40%, 50%, 75%, 80%, 85%, 90%, 95%, 98%, or 100%.

By "reference" is meant a standard or control condition, e.g., a wildtype or nonmutated protein or polynucleotide.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

A compound or antibody that "specifically binds" refers to one that recognizes and binds to a polypeptide, such as a virus polypeptide, peptide, or vaccine product, but which does not substantially recognize and bind to other molecules in a sample, for example, a biological sample, which naturally includes a polypeptide, such as a virus polypeptide or peptide.

Nucleic acid molecules useful in the methods described herein include any nucleic acid molecule that encodes a polypeptide as described, or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pairing to form a double-stranded molecule between complementary polynucleotide sequences (e.g., a gene), or portions thereof, under various conditions of stringency. (See, e.g., Wahl, G. M. and S. L. Berger, (1987), *Methods Enzymol.,* 152:399; Kimmel, A. R., (1987), *Methods Enzymol.* 152:507).

By way of example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations of these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations of these conditions will be readily apparent to those skilled in the art. Hybridization techniques are well known to those skilled in the art and are described, for example, in Benton and Davis (Science 196: 180, 1977); Grunstein and Hogness (*Proc. Natl. Acad. Sci., USA* 72:3961, 1975); Ausubel et al. (*Current Protocols in Molecular Biology, Wiley Interscience, New York,* 2001); Berger and Kimmel (*Guide to Molecular Cloning Techniques,* 1987, Academic Press, New York); and Sambrook et al., *Molecular Cloning: A Laboratory Manual,* Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, or at least 80% or 85%, or at least or equal to 90%, 95% or even 99% identical at the amino acid level or nucleic acid to the sequence used for comparison.

"Sequence identity" refers to the similarity between amino acid or nucleic acid sequences that is expressed in terms of the similarity between the sequences. Sequence identity is frequently measured in terms of percentage identity (or similarity or homology); the higher the percentage, the more similar the sequences are. Homologs or variants of a given gene or protein will possess a relatively high degree of sequence identity when aligned using standard methods. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence. In addition, other programs and alignment algorithms are described in, for example, Smith and Waterman, 1981, *Adv. Appl. Math.* 2:482; Needleman and Wunsch, 1970, *J Mol. Biol.* 48:443; Pearson and Lipman, 1988, *Proc. Natl. Acad. Sci. U.S.A.* 85:2444; Higgins and Sharp, 1988, *Gene* 73:237-244; Higgins and Sharp, 1989, *CABIOS* 5:151-153; Corpet et al., 1988, *Nucleic Acids Research* 16:10881-10890; Pearson and Lipman, 1988, *Proc. Natl. Acad. Sci. U.S.A.* 85:2444; and Altschul et al., 1994, *Nature Genet.* 6:119-129. The NCBI Basic Local Alignment Search Tool (BLAST™) (Altschul et al. 1990, *J Mol. Biol.* 215:403-410) is readily available from several sources, including the National Center for Biotechnology Information (NCBI, Bethesda, Md.) and on the Internet, for use in connection with the sequence analysis programs blastp, blastn, blastx, tblastn and tblastx.

By "subject" is meant a vertebrate animal, e.g., a mammal, including, but not limited to, a human, a non-human primate, or a non-human animal or mammal, such as a bovine, equine, canine, ovine, or feline mammal, or a sheep, goat, llama, camel, or a rodent (rat, mouse), gerbil, or hamster. A "subject" may also refer to anon-human animal, or to an avian vertebrate animal.

Non-human subjects or non-human animal subjects may also be referred to as "veterinary subjects." In a nonlimiting example, a subject is one who is infected with a pathogen, such as influenza virus, e.g., an H1, H2, H3, H5, or H7 virus, or IBV, or who is at risk of infection by such virus, or who is susceptible to such infection. In some aspects as described herein, the subject is a human subject, such as a patient. In some aspects as described herein, the subject is a non-human subject, such as a non-human animal subject or a veterinary subject.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or greater, consecutively, such as to 100 or greater, inclusive of the first and last values and those in between.

As used herein, the terms "treat," treating," "treatment," and the like refer to reducing, diminishing, decreasing, abating, abrogating, alleviating, ameliorating, or eliminating, a disease, condition, disorder, or pathology, and/or symptoms associated therewith. While not intending to be limiting, "treating" typically relates to a therapeutic intervention that occurs after a disease, condition, disorder, or pathology, and/or symptoms associated therewith, have begun to develop so as to reduce the severity of the disease, etc., and the associated signs and symptoms. It will be appreciated that, although not precluded, treating a disorder or condition does not require that the disease, condition, disorder, pathology, or the symptoms associated therewith, be completely eliminated.

As used herein, the terms "prevent," "preventing," "prevention," "prophylactic treatment" and the like, refer to inhibiting or blocking a disease state, or the full or full-blown development of a disease in a subject, or reducing the probability of developing a disease, disorder or condition in a subject, who does not have, but is at risk of developing, or is susceptible to developing, a disease, disorder, or condition.

As referred to herein, a "transformed" cell is a cell into which a nucleic acid molecule or polynucleotide sequence has been introduced by molecular biology techniques. As used herein, the term "transformation" encompasses all techniques by which a nucleic acid molecule or polynucleotide may be introduced into such a cell, including transfection with viral vectors, transformation with plasmid vectors, and introduction of naked nucleic acid (DNA or RNA) by electroporation, lipofection, and particle gun acceleration.

By "vaccine" is meant a preparation of immunogenic material (e.g., protein or nucleic acid), such as a protein or peptide antigen, capable of stimulating (eliciting) an immune response, administered to a subject to treat a disease, condition, or pathology, or to prevent or protect against a disease, condition, or pathology, such as an infectious disease, e.g., a virus infection. The immunogenic material may include, for example, attenuated or killed microorganisms (such as attenuated viruses), or antigenic proteins, peptides or DNA derived from such microorganisms. Vaccines may elicit a prophylactic (preventative) immune response in the subject; they may also elicit a therapeutic response immune response in a subject. As mentioned above, methods of vaccine administration vary according to the vaccine, and can include routes or means, such as inoculation (intravenous or subcutaneous injection), ingestion, inhalation, or other forms of administration as known and practiced in the medical art. Inoculations can be delivered by any of a number of routes, including parenteral, such as intravenous, subcutaneous or intramuscular. Vaccines may also be administered with an adjuvant to boost the immune response. Vaccines may be administered to human subjects, non-human subjects, or veterinary subjects.

As used herein, a "vector" refers to a nucleic acid (polynucleotide) molecule into which foreign nucleic acid can be inserted without disrupting the ability of the vector to replicate in and/or integrate into a host cell. A vector can include nucleic acid sequences that permit it to replicate in a host cell, such as an origin of replication. An insertional vector can insert itself into a host nucleic acid. A vector can also include one or more selectable marker genes and other genetic elements. An expression vector is a vector that contains the necessary regulatory sequences to allow transcription and translation of inserted gene or genes in a host cell. In some embodiments of the present disclosure, the vector encodes an influenza HA, NA or M1 protein. In some embodiments, the vector is the pTR600 expression vector (U.S. Patent Application Publication No. 2002/0106798; Ross et al., 2000, *Nat Immunol.* 1(2):102-103; and Green et al., 2001, *Vaccine* 20:242-248).

By "virus-like particle (VLP)" is meant virus particles made up of one of more viral structural proteins, but lacking the viral genome. Because VLPs lack a viral genome, they are non-infectious and yield safer and potentially more-economical vaccines and vaccine products. In addition, VLPs can often be produced by heterologous expression and can be easily purified. Most VLPs comprise at least a viral core protein that drives budding and release of particles from a host cell. One example of such a core protein is influenza M1. In some embodiments herein, an influenza VLP comprises the HA, NA and M1 proteins. As described herein, influenza or IBV VLPs can be produced by transfection of host cells with plasmids encoding the HA, NA and M1 proteins. After incubation of the transfected cells for an appropriate time to allow for protein expression (such as for approximately 72 hours), VLPs can be isolated from cell culture supernatants. By way of example, a protocol for purifying or isolating influenza VLPs from cell supernatants involves low speed centrifugation (to remove cell debris), vacuum filtration and ultracentrifugation of the VLPs through 20% glycerol. A virus-like particle may also include a subviral particle (SVP), which is typically smaller in size than a virus and constitutes a particle without a virus capsid or genome.

Unless specifically stated or obvious from context, as used herein, the term "or" is understood to be inclusive. Unless specifically stated or obvious from context, as used herein, the terms "a", "an", and "the" are understood to be singular or plural. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description.

Unless specifically stated or obvious from context, as used herein, the term "about" is understood as within a range of normal tolerance in the art, for example within 2 standard deviations of the mean. About may be understood as being within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIGS. 1A-1F show the amino acid sequences of representative hemagglutinin (HA) polypeptides (proteins) of influenza A virus strains, namely, H1, H2, H3, H5, or H7, or a representative avian infectious bronchitis virus (IBV) HA polypeptide, that are broadly reactive immunogens that elicit an immune response against influenza virus HA protein or IBV HA protein, respectively. Nucleic acid sequences encoding these polypeptides can be used to generate virus-like particles (VLPs) containing the influenza virus protein antigens or the IBV protein antigen, which are used as immunogens/vaccines to generate neutralizing antibodies in immunized subjects. FIG. 1A provides the amino acid sequence of H1 influenza HA antigen, Y3 (SEQ ID NO: 1). FIG. 1B provides the amino acid sequence of H2 influenza HA antigen, Z10 (SEQ ID NO: 2). FIG. 1C provides the amino acid sequence of H3 influenza HA antigen, J3 (SEQ ID NO: 3). FIG. 1D provides the amino acid sequence of H5 influenza HA antigen, IAN3 (SEQ ID NO: 4). FIG. 1E provides the amino acid sequence of H7 influenza HA antigen, Q6 (SEQ ID NO: 5). FIG. 1F provides the amino acid sequence of IBV HA antigen, B14 (SEQ ID NO: 6).

FIGS. 2A and 2B show the amino acid sequences of representative influenza virus neuraminidase (NA) antigens (polypeptides/proteins) that are broadly reactive immunogens that elicit an immune response against viral NA protein. Nucleic acid sequences encoding these NA polypeptides can be used to generate virus-like particles (VLPs) containing the virus protein antigen, which are used as immunogens/vaccines to generate neutralizing antibodies in immunized subjects. FIG. 2A provides the amino acid sequence of neuraminidase N1 NA-D antigen (SEQ ID NO: 7). FIG. 2B provides the amino acid sequence of neuraminidase N2 NA-A antigen (SEQ ID NO: 8).

DETAILED DESCRIPTION OF THE DISCLOSURE

Featured herein are synthetic (non-naturally occurring), immunogenic antigens, e.g., protein and glycoprotein antigens, derived from the influenza ("flu") hemagglutinin (HA) protein of influenza virus strains, e.g., H1, H2, H3, H5, or H7, or from avian infectious bronchitis virus (IBV), that elicit a potent, broadly reactive and long-lasting immune response in a subject. In an embodiment, the subject is a human subject. In an embodiment, the subject is an avian subject. In an embodiment, the synthetic (non-naturally occurring), immunogenic antigen, e.g., protein and glycoprotein antigen, is derived from the virus neuraminidase (NA) protein. Such immunogenic antigens are also referred to as "immunogens" herein.

Provided are broadly reactive immunogens that protect against disease caused by the influenza strains, such as H1, H2, H3, H5, or H7, or against IBV. In an embodiment, fully synthetic protein antigens are featured, such as influenza virus HA protein antigens or IBV protein antigen. Such HA antigens are synthetic proteins not found in nature, yet they retain all of the functions of a natural influenza virus or IBV HA protein and are immunogenic, i.e., they can elicit an immune response, in particular, a broadly active immune response in the form of neutralizing antibodies and/or reactive T lymphocytes, following administration or delivery to, or introduction into, a subject, especially for influenza virus antigen immunogens. Also provided are immunogenic compositions, e.g., vaccines, comprising the synthetic virus protein antigens, or nucleic acids encoding the antigens.

An HA amino acid sequence and a protein antigen having such sequence are particularly for use as an immunogen, or in an immunogenic composition, e.g., a vaccine, that elicits a broadly reactive immune response in a subject, particularly a human subject, to whom the composition, or vaccine, is administered. The synthetic antigens are designed to generate a broadly active immune response, particularly in the form of neutralizing antibodies, along with a cellular immune response in some cases, in a subject. In an embodiment, the subject is a human subject. In an embodiment, especially for an IBV immunogenic antigen, the subject is an avian subject. Such antigens are beneficial as immunogens, which elicit an immune response (e.g., production of neutralizing antibodies and/or a cellular immune response) against the virus, in particular, in cases in which more than one strain of virus co-circulate at a given time. By way of example, the broadly reactive influenza immunogenic antigens can be derived from influenza virus that frequently mutates parts of its genome to escape immune pressure, and as a consequence, evades immune surveillance in a subject whose immune system is not primed or stimulated to generate antibodies against antigenic epitopes (determinants) on the virus antigens following infection. Thus, the synthetic influenza virus antigens, e.g., H1, H2, H3, H5, or H7 HA antigen, comprise amino acid (or polynucleotide) sequences that will elicit greater numbers of neutralizing antibodies (and/or an improved cellular immune response) against potential influenza virus variants exhibiting antigenic drift compared with wild-type antigen sequences.

An HA immunogenic protein, or immunogen, of H1, H2, H3, H5, H7, or IBV as described herein can be employed in an immunogenic composition or as a vaccine that may afford protection against many virus strains over time. The broadly reactive virus antigen immunogens and vaccines described herein are advantageous in that they are designed to provide broader and longer-lasting protection against several different viral (e.g., influenza virus or IBV) strains (or clades), such as those arising in different areas.

The immunogenic influenza or IBV virus HA antigens described herein may be used in immunogenic compositions (e.g., vaccines) that can afford protective immunity against influenza virus or IBV infection and disease in a subject. The protective immunity is provided in the subject through the elicitation of broadly reactive, anti-HA specific antibody or cellular immune responses that protect the subject against virus strains that may have mutated or experienced antigenic drift.

Influenza Virus

Influenza viruses are segmented negative-strand RNA viruses that belong to the Orthomyxoviridae family. There are three types of Influenza viruses: types A, B and C. Influenza A viruses infect a wide variety of birds and mammals, including humans, horses, marine mammals, pigs, ferrets, and chickens. In animals, most influenza A viruses cause mild localized infections of the respiratory and intestinal tract. However, highly pathogenic influenza A strains, such as, for example, the H1N1 ("H1") or H5N1 ("H5"), or H7, or H9 strains, as well as IBV, cause systemic infections in poultry in which mortality may reach 100%. Animals infected with influenza A often act as a reservoir for the influenza viruses and certain subtypes have been shown to cross the species barrier to humans in whom they can cause severe disease and devastating flu outbreaks that can lead to death of the infected human subjects.

Influenza A viruses can be classified into subtypes based on allelic variations in antigenic regions of two genes that encode surface glycoproteins, namely, hemagglutinin (HA) and neuraminidase (NA) which are required for viral attachment and cellular release, respectively. Currently, sixteen subtypes of HA (H1-H16) and nine NA (N1-N9) antigenic variants are known for influenza A virus. Previously, only three subtypes were known to circulate in humans (H1N1 or H1N2). However, in recent years, for example, the pathogenic H5N1 subtype of avian influenza A has been reported to cross the species barrier and infect humans as documented in Hong Kong in 1997 and 2003, leading to the death of several patients.

In humans, the avian influenza virus infects cells of the respiratory tract as well as the intestinal tract, liver, spleen, kidneys and other organs. Symptoms of avian influenza infection include fever, respiratory difficulties, including shortness of breath and cough, lymphopenia, diarrhea and difficulties regulating blood sugar levels. In contrast to seasonal influenza, the group most at risk is healthy adults, which make up the bulk of the population. Due to the high pathogenicity of certain avian influenza A subtypes, particularly H5N1, and their demonstrated ability to cross over to infect humans, there is a significant economic and public health risk associated with these viral strains, including a real epidemic and pandemic threat. Currently, no effective vaccines for H5N1 infection are available.

The influenza A virus genome encodes nine structural proteins and one nonstructural (NS1) protein with regulatory functions. The influenza virus segmented genome contains eight negative-sense RNA (nsRNA) gene segments (PB2, PB1, PA, NP, M, NS, HA and NA) that encode at least ten polypeptides, including RNA-directed RNA polymerase proteins (PB2, PB 1 and PA), nucleoprotein (NP), neuraminidase (NA), hemagglutinin, e.g., subunits HA1, frequently referred to as the "head" subunit; and HA2, frequently referred to as the "tail" or "stalk" subunit; the matrix proteins (M1 and M2); and the non-structural proteins (NS1 and NS2) (See, e.g., Krug et al., 1989, In: *The Influenza Viruses*, R. M. Krug, ed., Plenum Press, N.Y., pp. 89 152).

The ability of influenza virus to cause widespread disease is due to its ability to evade the immune system by undergoing antigenic change, which is believed to occur when a host is infected simultaneously with both an animal influenza virus and a human influenza virus. During mutation and reassortment in the host, the virus may incorporate an HA and/or NA surface protein gene from another virus into its genome, thereby producing a new influenza subtype and evading the immune system.

Because of antigenic variation (drift) in the circulating strains of influenza viruses, in particular, in the HA and NA proteins of the virus, the efficacy of immunogenic compositions, e.g., vaccines, against influenza virus has frequently been less than optimal and sub-par. The methods described herein provide broadly reactive HA or NA antigens that generate a broadly reactive immune response, particularly, in the form of neutralizing antibodies that bind to the viral antigens and neutralize the activity of the virus (e.g., its ability to infect cells), to treat influenza and its symptoms more effectively.

Influenza Virus Hemagglutinin (HA) and Neuraminidase (NA) Proteins

HA is a viral surface glycoprotein that generally comprises approximately 560 amino acids (e.g., 566 amino acids) and represents 25% of the total virus protein. As described herein, HA is a protein antigen that is highly useful as an immunogen because it contains a diverse repertoire of epitopes against which antibodies are generated in a subject or host that encounters the HA antigen of influenza viruses during infection.

HA is responsible for adhesion of the viral particle to, and its penetration into, a host cell, particularly, in the respiratory epithelium, in the early stages of infection. Cleavage of the virus HA0 precursor into the HA1 and HA2 sub-fragments is a necessary step for the virus to infect a cell. Thus, cleavage is required to convert new virus particles in a host cell into virions capable of infecting new cells. Cleavage is known to occur during transport of the integral HA0 membrane protein from the endoplasmic reticulum of the infected cell to the plasma membrane. During transport, HA undergoes a series of co- and post-translational modifications, including proteolytic cleavage of the precursor HA into the amino-terminal fragment HA1 ("head") and the carboxy terminal HA2 ("tail" or "stalk"). One of the primary difficulties in growing influenza strains in primary tissue culture or established cell lines arises from the requirement for proteolytic cleavage activation of the influenza hemagglutinin in the host cell.

Although it is known that an uncleaved HA can mediate attachment of the virus to its neuraminic acid-containing receptors on a cell surface, it is not capable of the next step in the infectious cycle, which is fusion. It has been reported that exposure of the hydrophobic amino terminus of HA2 by cleavage is required so that it can be inserted into the target cell, thereby forming a bridge between the virus and the target cell membranes. This process is followed by fusion of the two membranes and entry of the virus into the target cell.

Proteolytic activation of HA involves cleavage at an arginine residue by a trypsin-like endoprotease, which is often an intracellular enzyme that is calcium-dependent and has a neutral pH optimum. Since the activating proteases are cellular enzymes, the infected cell type determines whether the HA is cleaved. The HA of the mammalian influenza viruses and the nonpathogenic avian influenza viruses are susceptible to proteolytic cleavage only in a restricted number of cell types. On the other hand, HA of pathogenic avian viruses among the H5 and H7 subtypes are cleaved by proteases present in a broad range of different host cells. Thus, there are differences in host range resulting from differences in hemagglutinin cleavability which are correlated with the pathogenic properties of the virus.

Neuraminidase (NA) is a second membrane glycoprotein of the influenza viruses. The presence of viral NA has been shown to be important for generating a multi-faceted protective immune response against an infecting virus. For most influenza A viruses, NA is 413 amino acids in length and is encoded by a gene of 1413 nucleotides. Nine different NA subtypes have been identified in influenza viruses (N1, N2, N3, N4, N5, N6, N7, N8 and N9), all of which have been found among wild birds. NA is involved in the destruction of the cellular receptor for the viral HA by cleaving terminal neuraminic acid (also called sialic acid) residues from carbohydrate moieties on the surfaces of infected cells. NA also cleaves sialic acid residues from viral proteins, thus preventing aggregation of viruses. Using this mechanism, it is hypothesized that NA facilitates the release of viral progeny by preventing newly formed viral particles from accumulating along the cell membrane, as well as by promoting transportation of the virus through the mucus present on the mucosal surface. NA is an important antigenic determinant that is subject to antigenic variation.

In addition to the surface proteins HA and NA, influenza virus comprises six additional internal genes, which give rise to eight different proteins, including polymerase genes PB1, PB2 and PA, matrix proteins M1 and M2, nucleoprotein (NP), and non-structural proteins NS1 and NS2 (See, e.g., Horimoto et al., 2001, *Clin Microbiol Rev.* 14(1):129-149).

For packaging into progeny virions, viral RNA is transported from the nucleus as a ribonucleoprotein (RNP) complex composed of the three influenza virus polymerase proteins, the nucleoprotein (NP), and the viral RNA, in association with the influenza virus matrix 1 (M1) protein and nuclear export protein (Marsh et al., 2008, *J Virol,* 82:2295-2304). The M1 protein that lies within the envelope is thought to function in assembly and budding. A limited number of M2 proteins are integrated into the virions (Zebedee, 1988, *J Virol.* 62:2762-2772). These M2 proteins form tetramers having H+ ion channel activity, and when activated by the low pH in endosomes, acidify the inside of the virion, thus facilitating its uncoating (Pinto et al., 1992, *Cell* 69:517-528). Amantadine is an anti-influenza drug that prevents viral infection by interfering with M2 ion channel activity, thus inhibiting virus uncoating.

NS1, a nonstructural protein, has multiple functions, including regulation of splicing and nuclear export of cellular mRNAs as well as stimulation of translation. The major function of NS1 seems to be to counteract the interferon activity of the host, since an NS1 knockout virus was viable, although it grew less efficiently than the parent virus in interferon-nondefective cells (Garcia-Sastre, 1998, *Virology* 252:324-330).

The NS2 nonstructural protein has been detected in virus particles (Richardson et al., 1991, *Arch. Virol.* 116:69-80; Yasuda et al., 1993, *Virology* 196:249-255). The average number of NS2 proteins in a virus particle was estimated to be 130-200 molecules. An in vitro binding assay has demonstrated direct protein-protein contact between M1 and NS2. NS2-M1 complexes have also been detected by immunoprecipitation in virus-infected cell lysates. The NS2 protein is thought to play a role in the export of the RNP from the nucleus through interaction with M1 protein (Ward et al., 1995, *Arch. Virol.* 140:2067-2073).

Coronavirus

Coronavirus (CoV) is a virus species of the subfamily Coronavirinae in the family Coronaviridae. Coronaviruses are enveloped viruses having a positive-sense, single-stranded RNA genome and a nucleocapsid of helical symmetry. The genome size of coronaviruses ranges from about 26 to 32 kilobases, the largest for an RNA virus. The name "coronavirus," which is derived from the Latin corona, meaning crown or halo, refers to the characteristic appearance of coronavirus virions under electron microscopy (EM). As seen under EM, these viruses have a fringe of large, bulbous surface protein projections that create an image reminiscent of a crown or a solar corona. This morphology is created by the viral spike (S) peplomers, which are proteins displayed on the surface of the virus and determine host tropism.

Proteins that contribute to the overall structure of all coronaviruses are the spike (S), envelope (E), membrane (M) and nucleocapsid (N). In the case of the Severe Acute Respiratory Syndrome (SARS) coronavirus, a defined receptor-binding domain on the S protein mediates the attachment of the virus to its cellular receptor, angiotensin-converting enzyme 2 (ACE2). Some coronaviruses (specifically the members of Betacoronavirus subgroup A) also have shorter spike-like protein projections called hemagglutinin esterase (HE).

Replication of coronavirus begins with virus entry into the cytoplasm of a cell in a membrane-protected microenvironment. Upon cell entry, the coronavirus particle is uncoated, and the RNA genome is deposited into the cytoplasm. The coronavirus genome has a 5' methylated cap and a 3' polyadenylated tail, which allows the RNA to attach to ribosomes for viral protein translation. The coronavirus genome encodes a replicase protein that allows the RNA viral genome to be transcribed into new RNA copies using the host cell's machinery. The replicase protein is the first protein to be synthesized intracellularly. Upon replication of the coronavirus RNA genome, a long polyprotein is formed to which all of the viral proteins are attached. The nonstructural coronavirus protease protein cleaves the proteins in the polyprotein chain into discrete virus proteins that are assembled into virus progeny in the infected cell.

Coronaviruses primarily infect the upper respiratory and gastrointestinal tracts of mammals and birds. A number of strains of coronaviruses also infect humans, e.g., human coronaviruses 229E, OC43, SARS-CoV, NL63, Hong Kong University 1 virus (HKU1), and Middle East Respiratory Syndrome (MERS)-CoV. Coronaviruses are believed to cause a significant percentage of all common colds in human adults and children. The major cold symptoms attributed to coronavirus infection (primarily in the winter and early spring seasons) include fever, throat congestion and adenoids. In addition, coronaviruses can cause either direct viral pneumonia or a secondary bacterial pneumonia, as well as bronchitis, either direct viral bronchitis or a secondary bacterial bronchitis. The highly publicized human coronavirus discovered in 2003, SARS-CoV, causes severe acute respiratory syndrome (SARS) and infects both the upper and lower respiratory tracts.

Since the early 1970s, coronaviruses have been reported to cause pathological conditions in veterinary medicine. Except for avian infectious bronchitis (caused by the coronavirus, avian infectious bronchitis virus (IBV)), the most prominent related diseases localize primarily in the intestine. Coronaviruses also cause diseases in farm animals and domesticated pets, some of which can be serious and threaten the farming industry. In chickens, IBV targets not only the respiratory tract but also the urogenital tract and can spread to different organs throughout the chicken's body. Economically significant coronaviruses of farm animals include porcine coronavirus (transmissible gastroenteritis coronavirus, TGE) and bovine coronavirus, which cause diarrhea in young animals. Coronaviruses also affect feline animals. Feline enteric coronavirus is a pathogen of minor clinical significance; however, spontaneous mutation of this virus can result in feline infectious peritonitis (FIP), a disease associated with high mortality. Similarly, coronaviruses infect ferrets; ferret enteric coronavirus causes a gastrointestinal syndrome known as epizootic catarrhal enteritis (ECE). In addition, a more lethal version of the virus, ferret systemic coronavirus (FSC), can cause a systemic infection in ferrets, similar to that of FIP in cats. In dogs, canine coronavirus (CCoV) can present in a form that causes mild gastrointestinal disease and in a form that causes respiratory disease. Mouse hepatitis virus (MHV) is a coronavirus that causes an epidemic murine illness with high mortality, especially among colonies of laboratory mice. An HKU2-related bat corona virus called SADS-CoV causes diarrhea in pigs.

Viral Proteins and Virus-Like Particles (VLPs)

Provided are non-naturally occurring, broadly reactive influenza (e.g., H1, H2, H3, H5, or H7) or IBV HA immunogenic polypeptides (immunogens) and virus-like particles (VLPs) comprising an influenza virus or IBV HA immunogen containing diverse epitopes (antigenic determinants) that endow the HA antigen with the ability to generate a broadly active immune response against influenza and its symptoms, either prophylactic or therapeutic, following administration and delivery to a susceptible subject. By way of example, representative influenza or IBV virus HA immunogenic antigen sequences are presented in FIGS. TA-1F (SEQ ID NOs: 1-6) herein. By way of further example, representative NA (e.g., influenza virus NA) immunogenic antigen sequences are presented in FIGS. 2A (SEQ ID NO: 7) and 2B (SEQ ID NO: 8) herein. In particular embodiments, the broadly reactive HA or NA polypeptides are administered as part of a VLP.

It will be understood that the influenza virus immunogens and sequences described and provided herein are non-naturally occurring and broadly reactive, whether or not these characteristics and features are explicitly stated. It will be further understood that the antigen proteins described herein and used as immunogens are non-naturally occurring or synthetic antigens that elicit an immune response, e.g., neutralizing antibodies and/or a cellular immune response, in a subject.

The influenza VLPs include the viral HA, NA and M1 proteins. The production of influenza VLPs has been described in the art and is within the skill and expertise of one of ordinary skill in the art. Briefly, and as described, influenza VLPs can be produced by transfection of host cells with one or more plasmids containing polynucleotide sequences that encode the HA, NA and M1 proteins. After incubation of the transfected cells for an appropriate time to allow for protein expression (such as for approximately 72 hours), VLPs can be isolated from cell culture supernatants. Influenza VLPs can be purified from cell supernatants using procedures practiced in the art, for example, VLPs can be isolated by low speed centrifugation (to remove cell debris), vacuum filtration and ultracentrifugation through 20% glycerol. In an embodiment, VLPs containing broadly reactive antigens derived from other pathogens can also be produced, isolated and used as immunogens or in immunogenic compositions.

The influenza VLPs can be used as influenza vaccines to elicit an immune response against the H1, H2, H3, H5 and H7 influenza viruses. In addition, the VLPs can be used as IBV vaccines to elicit an immune response against IBV. In particular, the component, broadly reactive influenza HA polypeptides of the vaccines (or VLPs) contain antigenic determinants that are broadly reactive and serve to elicit an immune response in a subject (e.g., the production of neutralizing antibodies and/or activated T-cells) that can treat a virus-infected subject (e.g., neutralize the infecting virus) and/or protect a subject against full-blown virus infection or the signs and symptoms thereof.

In an embodiment, the antigen sequence of a broadly reactive and immunogenic influenza or IBV antigen as described herein, such as an H1, H2, H3, H5, H7, or IBV HA antigen, contains a diverse repertoire of epitopic determinants that can reflect antigenic drift and sequence variability in the virus's antigenic proteins. In particular, an influenza or IBV virus HA antigen as described herein can comprise an amino acid sequence that contains antigenic determinants (epitopes) derived from sequence diverse influenza or IBV virus strains, including drift variants, against which broadly reactive neutralizing antibodies can be raised, especially when the antigen is used as an immunogenic product, (an immunogen), e.g., an antiviral vaccine, that is introduced into a subject.

Because the broadly reactive influenza or IBV HA antigens and the sequences thereof as described herein and used as an immunogen or immunogenic composition, such as a vaccine, elicit a broadly reactive immune response in an immunocompetent subject, they provide a superior immunogenic product (e.g, a vaccine) that captures the antigenic determinants of different influenza isolates (subtypes or strains), against which broadly active immune responses (e.g., broadly active neutralizing antibodies and/or cellular immune responses) are generated. It is noted that the terms "broadly active" and "broadly reactive" are used synonymously herein.

In an embodiment, the influenza or IBV virus antigen as described herein is a polypeptide or peptide antigen of the virus which currently causes disease or infection and its symptoms, such as influenza, flu, or infectious bronchitis. In another embodiment, the influenza or IBV virus antigen is a polypeptide or peptide antigen which may cause future disease and infection. In an embodiment, the influenza or IBV virus antigen is a polynucleotide sequence. In an embodiment, the influenza or IBV virus antigen is a polynucleotide sequence that encodes a polypeptide or peptide antigen as described herein. By way of example, representative broadly reactive influenza or IBV virus HA immunogenic sequences are shown in FIGS. 1A-1F (SEQ ID NOs: 1-6) and supra. Representative broadly reactive influenza virus NA immunogenic sequences are shown in FIGS. 2A (SEQ ID NO: 7) and 2B (SEQ ID NO: 8) and supra.

In another embodiment, the influenza or IBV immunogen sequence described herein is expressed in a cell as a polypeptide, protein, or peptide. In an embodiment, the influenza or IBV immunogen is isolated and/or purified. In an embodiment, the immunogen is formulated for administration to a subject in need. In an embodiment, the immunogen is administered to a subject in need thereof in an effective amount to elicit an immune response in the subject. In an embodiment, the immune response elicits neutralizing antibodies. In an embodiment, a cellular immune response is elicited. In an embodiment, the immune response is prophylactic or therapeutic.

In an embodiment, a non-naturally occurring influenza virus or IBV immunogen (immunogen sequence), e.g., a vaccine, is provided that elicits a broadly reactive immune response in a subject following introduction, administration, or delivery of the immunogen to the subject. The route of introduction, administration, or delivery is not limited and may include, for example, intravenous, subcutaneous, intramuscular, oral, etc. routes. The vaccine may be therapeutic (e.g., administered to a subject following a symptom of disease (flu or bronchitis) caused by the influenza virus or IBV, or it may be prophylactic (protective), (e.g., administered to a subject prior to the subject having or expressing a symptom of disease (flu or bronchitis), or full-blown disease, caused by the virus.

In an embodiment, the final amino acid sequence of the viral antigen, e.g., HA or NA, is reverse translated and optimized for expression in mammalian cells. As will be appreciated by the skilled practitioner in the art, optimization of the nucleic acid sequence includes optimization of the codons for expression of a sequence in mammalian cells and RNA optimization (such as RNA stability).

In an embodiment, an isolated nucleic acid molecule (polynucleotide) comprising a nucleotide sequence encoding a polypeptide or peptide antigen, such as an influenza virus or IBV HA polypeptide (or HA1 or HA2 polypeptide), is provided. In certain embodiments, the nucleotide sequence encoding the HA polypeptide is at least 94%, at least 95%, at least 96%, at least 97%, at least 98% or at least 99% identical to a polynucleotide encoding an HA polypeptide (or HA1 or HA2 polypeptide) sequence shown in FIGS. 1A-1F (SEQ ID NOs: 1-6) and as shown supra.

In other embodiments, the nucleotide sequence encoding an influenza virus or IBV HA polypeptide (or HA1 or HA2 polypeptide) that is at least 90%, at least 91%, at least 92%, at least 93%, at least 94%, at least 95%, at least 96%, at least 97%, at least 98%, or at least 99% identical to a polynucleotide encoding an influenza virus or IBV HA polypeptide (or HA1 or HA2 polypeptide) sequence shown in FIGS. 1A-1F (SEQ ID NOs: 1-6) and supra lacks the start codon encoding an N-terminal methionine.

In an embodiment, an isolated nucleic acid molecule (polynucleotide) comprising a nucleotide sequence encoding a polypeptide or peptide antigen, such as an influenza virus NA polypeptide (e.g., N1 or N2 polypeptide), is provided. In certain embodiments, the nucleotide sequence encoding the NA polypeptide is at least 94%, at least 95%, at least 96%, at least 97%, at least 98% or at least 99% identical to a polynucleotide encoding an NA polypeptide (or N1 or N2 polypeptide) sequence shown in FIGS. 2A (SEQ ID NO: 7) and 2B (SEQ ID NO: 8) and as shown supra.

In other embodiments, the nucleotide sequence encoding an influenza virus NA polypeptide (or N1 or N2 polypeptide) that is at least 90%, at least 91%, at least 92%, at least 93%, at least 94%, at least 95%, at least 96%, at least 97%, at least 98%, or at least 99% identical to a polynucleotide encoding an influenza virus NA polypeptide (or N1 or N2 polypeptide) sequence shown in FIGS. 2A (SEQ ID NO: 7) and 2B (SEQ ID NO: 8) and supra lacks the start codon encoding an N-terminal methionine.

Vectors containing a nucleotide sequence encoding a non-naturally occurring, broadly reactive polypeptide or peptide antigen, such as an influenza or IBV HA polypeptide, (or HA1 or HA2 polypeptide), are provided. In some embodiments, the vectors comprise a nucleotide sequence encoding the polypeptide or peptide antigen, such as an influenza H3 HA polypeptide antigen, that is at least 94%, at least 95%, at least 96%, at least 97%, at least 98% or at least 99% identical to a polynucleotide encoding an HA polypeptide (or HA1 or HA2 polypeptide) sequence shown in FIGS. 1A-1F (SEQ ID NOs: 1-6) and supra. In some embodiments, the vector further includes a promoter operably linked to the nucleotide sequence encoding the HA polypeptide (or HA1 or HA2 polypeptide). In a particular embodiment, the promoter is a cytomegalovirus (CMV) promoter. In some embodiments, the nucleotide sequence of the vector is at least 85%, at least 90%, at least 95%, at least 98% or at least 99% identical to a polynucleotide encoding an HA polypeptide (or HA1 or HA2 polypeptide) sequence shown in FIGS. 1A-1F (SEQ ID NOs: 1-6) and supra. In particular embodiments, the nucleotide sequence of the vector comprises the polynucleotide encoding an HA polypeptide (or HA1 or HA2 polypeptide) sequence shown in FIGS. 1A-1F (SEQ ID NOs: 1-6) and supra. In embodiments, the vector is a prokaryotic or eukaryotic vector. In an embodiment, the vector is an expression vector, such as a eukaryotic (e.g., mammalian) expression vector. In another embodiment, the vector is a plasmid (prokaryotic or bacterial) vector. In another embodiment, the vector is a viral vector.

The vectors used to express an influenza virus antigen, e.g., an H1, H2, H3, H5, or H7 viral protein, or an IBV antigen, such as the HA protein, as described herein may be any suitable expression vectors known and used in the art. The vectors can be, for example, mammalian expression vectors or viral vectors. In some embodiments, the vector is the pTR600 expression vector (U.S. Patent Application Publication No. 2002/0106798, herein incorporated by reference; Ross et al., 2000, *Nat Immunol.* 1(2):102-103; and Green et al., 2001, *Vaccine* 20:242-248).

Provided are influenza virus- or IBV-derived, non-naturally occurring polypeptide antigens, e.g., H1, H2, H3, H5, or H7 influenza HA polypeptide antigens, or HA1 or HA2 polypeptide antigens, (or IBV HA polypeptide antigen) produced by transfecting a host cell with an expression vector as known and used in the art under conditions sufficient to allow for expression of the polypeptide, e.g., an HA, HA1, or HA2 polypeptide, in the cell. Isolated cells containing the vectors are also provided.

Also provided are non-naturally occurring, broadly reactive influenza virus or IBV antigen polypeptides as described herein, such as broadly reactive H1, H2, H3, H5, or H7 influenza HA polypeptides or IBV HA polypeptide. In certain embodiments, the amino acid sequence of the polypeptide is at least 95% to 99% (inclusive) identical to the amino acid sequence of an HA, HA1, or HA2 polypeptide as shown in FIGS. 1A-1F (SEQ ID NOs: 1-6) and supra. In particular embodiments, the amino acid sequence of the influenza HA, HA1, or HA2 polypeptide that is at least 95% to 99% (inclusive) identical to the amino acid sequence of an HA, HA1, or HA2 polypeptide shown in FIGS. 1A-1F (SEQ ID NOs: 1-6) and supra lacks the N-terminal methionine residue. In a particular embodiment, the amino acid sequence of the influenza HA polypeptide is at least 95% to 99% (inclusive) identical to the amino acid sequence of the HA polypeptides shown in FIGS. 1A-1F (SEQ ID NOs: 1-6) and supra.

Also provided are non-naturally occurring, broadly reactive influenza virus NA antigen polypeptides as described herein, such as broadly reactive H1, H2, H3, H5, or H7 influenza NA polypeptides. In certain embodiments, the amino acid sequence of the polypeptide is at least 95% to 99% (inclusive) identical to the amino acid sequence of an NA, (e.g., N1 or N2) polypeptide as shown in FIGS. 2A (SEQ ID NO: 7) and 2B (SEQ ID NO: 8) and supra. In particular embodiments, the amino acid sequence of the influenza NA (e.g., N1 or N2) polypeptide that is at least 95% to 99% (inclusive) identical to the amino acid sequence of an NA (e.g., N1 or N2) polypeptide shown in FIGS. 2A (SEQ ID NO: 7) and 2B (SEQ ID NO: 8) and supra lacks the N-terminal methionine residue. In a particular embodiment, the amino acid sequence of the influenza NA polypeptide is at least 95% to 99% (inclusive) identical to the amino acid sequence of the NA polypeptides shown in FIGS. 2A (SEQ ID NO: 7) and 2B (SEQ ID NO: 8) and supra.

In some embodiments, fusion proteins comprising the broadly reactive influenza virus or IBV antigen polypeptides described herein, e.g., without limitation, the HA or NA polypeptides disclosed herein, are also provided. In some embodiments, the influenza or IBV HA polypeptide can be fused to any heterologous amino acid sequence to form the fusion protein. By way of example, HA1 and HA2 polypeptides may be generated independently and then fused together to produce an influenza HA polypeptide antigen or an IBV HA polypeptide antigen. (FIGS. 1A-1F (SEQ ID NOs: 1-6) and supra).

Also provided are virus-like particles (VLPs), in particular, H1, H2, H3, H5, H7 influenza VLPs, or IBV VLPs, containing a broadly reactive protein antigen, e.g., HA or NA protein, as described herein. In certain embodiments, the HA protein of the VLP is at least or equal to 94%, at least or equal to 95%, at least or equal to 96%, at least or equal to 97%, at least or equal to 98%, at least or equal to 99% or 100% identical to the influenza virus or IBV HA proteins as shown in FIGS. 1A-1F (SEQ ID NOs: 1-6) and supra. The virus or influenza VLPs can further include any additional viral or influenza proteins necessary to form the virus particle.

In certain embodiments, the virus or influenza VLPs further include influenza neuraminidase (NA) protein, influenza matrix (M1) protein, or both. In certain embodiments, the NA protein (e.g., N1 or N2) of the VLP is at least or equal to 94%, at least or equal to 95%, at least or equal to 96%, at least or equal to 97%, at least or equal to 98%, at least or equal to 99% or 100% identical to the NA protein as shown in FIGS. 2A (SEQ ID NO: 7) and 2B (SEQ ID NO: 8) and supra.

Also provided is an influenza VLP containing an H1, H2, H3, H5, or H7 influenza virus HA, HA1, or HA2 polypeptide, or an IBV HA VLP, as described herein, produced by transfecting a host cell with a vector containing a polynucleotide encoding the HA, HA1, or HA2 polypeptide. Also provided in a certain embodiment is an influenza VLP containing an influenza HA polypeptide, or HA1 or HA2 polypeptide, as described herein, produced by transfecting a host cell with a vector encoding the influenza virus HA, HA1, or HA2 polypeptide, a vector encoding an influenza NA protein and a vector encoding an influenza M1 protein, under conditions sufficient to allow for expression of the influenza virus HA, NA and M1 proteins. Such VLPs comprising the sequences as presented in FIGS. 1A-1E (SEQ ID NOs: 1-5) and used as immunogens generate antibodies having high hemagglutinin inhibition (HAI) titers against different strains of the influenza virus types described herein.

Collections of plasmids (vectors) are also contemplated. In certain embodiments, the collection of plasmids includes a plasmid encoding an influenza virus NA, a plasmid encoding an influenza MA, and a plasmid encoding a broadly reactive influenza virus HA protein as described herein. In some embodiments, the nucleotide sequence encoding an influenza HA protein of the HA-encoding plasmid is at least 94%, at least 95%, at least 96%, at least 97%, at least 98% or at least 99% identical to a polynucleotide encoding an HA amino acid sequence as shown in FIGS. 1A-1E (SEQ ID NOs: 1-5). In some embodiments, the nucleotide sequence encoding a codon-optimized influenza HA protein of the HA-encoding plasmid is at least 94%, at least 95%, at least 96%, at least 97%, at least 98% or at least 99% identical to a polynucleotide encoding an influenza HA amino acid sequence as shown in FIGS. 1A-1E (SEQ ID NOs: 1-5) and supra. In another embodiment, the collection of plasmids contains a plasmid encoding a broadly reactive IBV HA protein as described herein, comprising a polynucleotide encoding an HA amino acid sequence as shown in FIG. 1F (SEQ ID NO: 6) and supra, or a nucleotide sequence encoding a codon-optimized influenza IBV HA protein.

In the context of the present disclosure, "broadly reactive" or "broadly active" means that the influenza virus or IBV protein (e.g., an H1, H2, H3, H5, H7, or IBV HA protein sequence) is immunogenic and contains a diversity of epitopes (antigenic determinants) that elicit in a subject an immune response (e.g., neutralizing antibodies directed against the epitopes contained in the broadly reactive protein immunogen, frequently accompanied by a T-cell response) sufficient to treat disease or infection, and/or to inhibit, neutralize, or prevent infection, caused by most or all of the influenza viruses, or IBV, within a specific subtype, or by related virus strains. In embodiments, the broadly reactive H1, H2, H3, H5, or H7 influenza virus-derived antigen protein, e.g., HA protein, can elicit a protective immune response against most or all known H1, H2, H3, H5, or H7 influenza virus isolates, such as about 70%, about 75%, about 80%, about 85%, about 90%, about 95%, or about 96%-99% of the known H1, H2, H3, H5, or H7 influenza virus isolates. In another embodiment, the broadly reactive IBV-derived antigen protein, e.g., HA protein, can elicit a protective immune response against most or all known IBV isolates, such as about 70%, about 75%, about 80%, about 85%, about 90%, about 95%, or about 96%-99% of the known IBV isolates Compositions and Pharmaceutical Compositions for Administration Compositions comprising a broadly reactive influenza or IBV HA protein, or a fusion protein or VLP comprising such a broadly reactive influenza or IBV HA protein as described herein are provided. In some embodiments, the compositions further comprise a pharmaceutically acceptable carrier, excipient, or vehicle. In some embodiments, an adjuvant (a pharmacological or immunological agent that modifies or boosts an immune response, e.g. to produce more antibodies that are longer-lasting) is also employed. For example, without limitation, the adjuvant can be an inorganic compound, such as alum, aluminum hydroxide, or aluminum phosphate; mineral or paraffin oil; squalene; detergents such as Quil A; plant saponins; Freund's complete or incomplete adjuvant, a biological adjuvant (e.g., cytokines such as IL-1, IL-2, or IL-12); bacterial products such as killed *Bordetella pertussis*, or toxoids; or immuno-stimulatory oligonucleotides (such as CpG oligonucleotides).

Compositions and preparations (e.g., physiologically or pharmaceutically acceptable compositions) containing the non-naturally occurring, broadly reactive influenza virus or IBV HA polypeptides and influenza virus-like particles (VLPs) or IBV VLPs for parenteral administration include, without limitation, sterile aqueous or non-aqueous solutions, suspensions, and emulsions. Nonlimiting examples of non-aqueous solvents include propylene glycol, polyethylene glycol, vegetable oils, such as olive oil and canola oil, and injectable organic esters, such as ethyl oleate. Aqueous carriers include water, alcoholic/aqueous solutions, emulsions or suspensions, including saline and buffered media. Parenteral vehicles include, for example, sodium chloride solution, Ringer's dextrose, dextrose and sodium chloride, lactated Ringer's, or fixed oils. Intravenous vehicles include, for example, fluid and nutrient replenishers, electrolyte replenishers (such as those based on Ringer's dextrose), and the like. Preservatives and other additives may also be present in such compositions and preparations, such as, for example, antimicrobials, antioxidants, chelating agents, colorants, stabilizers, inert gases and the like.

Some of the compositions may potentially be administered as a pharmaceutically acceptable acid- or base-addition salt, formed by reaction with inorganic acids, such as hydrochloric acid, hydrobromic acid, perchloric acid, nitric acid, thiocyanic acid, sulfuric acid, and phosphoric acid, and organic acids, such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, tri-alkyl and aryl amines and substituted ethanolamines.

Provided herein are pharmaceutical compositions which include a therapeutically effective amount of a non-naturally occurring, broadly reactive influenza virus or IBV protein antigen, or influenza or IBV VLPs, alone, or in combination with a pharmaceutically acceptable carrier. In embodiments, the influenza virus antigens include those of the H1, H2, H3, H5, or H7 influenza viruses, or IBV, having the sequences as shown, for example, in FIGS. TA-1F (SEQ ID NOs: 1-6) and supra. Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid or aqueous solution, suspension, emulsion, dispersion, tablet, pill, capsule, powder, or sustained release formulation. A liquid or aqueous composition can be lyophilized and reconstituted with a solution or buffer prior to use. The composition can be formulated as a suppository, with traditional binders and carriers such as triglycerides. Oral formulations can include standard carriers, such as pharmaceutical grades of mannitol, lactose, starch, magnesium stearate, sodium saccharine, cellulose, and magnesium carbonate. Any of the commonly known pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used in the compositions and administration methods as described are normal saline and sesame oil.

Methods of Treatment, Administration and Delivery

Methods of treating a disease or infection, or symptoms thereof, caused by influenza virus (e.g., H1, H2, H3, H5, or H7 influenza viruses) or IBV are provided. The methods comprise administering a therapeutically effective amount of a broadly reactive immunogen as described herein or a pharmaceutical composition comprising the immunogen, or a vaccine (e.g., a VLP vaccine) as described herein to a subject (e.g., a mammal), in particular, a human subject, a non-human animal or veterinary subject, or an avian subject. One embodiment involves a method of treating a subject suffering from, or at risk of or susceptible to, disease or infection, or a symptom thereof, caused by influenza virus or by IBV. The method includes administering to the subject (e.g., a mammalian subject), an amount or a therapeutic amount of an immunogenic composition or a vaccine comprising a non-naturally occurring, broadly reactive influenza virus or IBV antigen polypeptide, such as the HA or NA polypeptides, or HA or NA VLPs, sufficient to treat the disease, infection, or symptoms thereof, caused by the influenza virus or IBV, under conditions in which the disease, infection, and/or the symptoms thereof are treated.

In an embodiment, the methods herein include administering to the subject (including a human subject or a non-human subject identified as being in need of such treatment) an effective amount of a non-naturally occurring, broadly reactive influenza virus antigen polypeptide, such as the H1, H2, H3, H5, or H7 influenza virus HA or NA polypeptide as described herein, or an IBV HA antigen polypeptide as described herein, or a vaccine, or a composition as described herein to produce an immune response. The treatment methods are suitably administered to subjects, particularly humans, suffering from, having, susceptible to, or at risk of having a disease, disorder, infection, or symptom thereof, e.g., flu or influenza, or infectious bronchitis. In embodiments, the treatment methods are also suitably administered to non-human subjects, such as non-human animal subjects, veterinary subjects, or avian subjects. Identifying a subject in need of such treatment can be based on the judgment of the subject or of a medical or veterinary health care professional and can be subjective (e.g. opinion) or objective (e.g. measurable by a test or diagnostic method). Briefly, the determination of those subjects who are in need of treatment or who are "at risk" or "susceptible" can be made by any objective or subjective determination by a diagnostic test (e.g., genetic test, enzyme or protein marker assay), marker analysis, family history, and the like, including an opinion of the subject or a health care provider. The non-naturally occurring, broadly reactive virus immunogens, such as the H1, H2, H3, H5, or H7 influenza virus HA or NA polypeptide, or the IBV HA polypeptide, immunogens and vaccines as described herein, may also be used in the treatment of any other disorders in which infection or disease caused by an H1, H2, H3, H5, or H7 influenza virus, respectively, or IBV, may be implicated. A subject undergoing treatment can be a non-human mammal, such as a veterinary subject, an avian subject, or a human subject (also referred to as a "patient").

In addition, prophylactic methods of preventing or protecting against a disease or infection, or symptoms thereof, caused by influenza virus, e.g., the H1, H2, H3, H5, or H7 influenza viruses, or IBV, are provided. Such methods comprise administering a therapeutically effective amount of a pharmaceutical composition comprising an H1, H2, H3, H5, or H7 influenza virus HA or NA polypeptide immunogenic composition or vaccine (e.g., an H1, H2, H3, H5, or H7 influenza virus VLP vaccine) as described herein to a subject (e.g., a mammal such as a human) in need, in particular, prior to infection of the subject or prior to onset of the disease, such as H3 virus-associated disease. In an embodiment, a therapeutically effective amount of a pharmaceutical composition comprising an IBV HA polypeptide immunogenic composition or vaccine such as described herein is administered to a subject in need.

In another embodiment, a method of monitoring the progress of an influenza virus infection or disease caused by H1, H2, H3, H5, or H7 influenza virus, or an IBV infection or disease caused by IBV, or of monitoring treatment of the influenza virus or IBV infection or disease is provided. The method includes determining a level of a diagnostic marker or biomarker (e.g., an influenza virus protein, such as H1, H2, H3, H5, or H7 HA or NA; or an IBV protein, such as IBV HA), or a diagnostic measurement (e.g., screening assay or detection assay) in a subject suffering from or susceptible to infection, disease or symptoms thereof associated with influenza virus or IBV, in which the subject has been administered an amount (e.g., a therapeutic amount) of a non-naturally occurring, broadly reactive influenza virus or IBV HA protein immunogen as described herein, or a vaccine as described herein, sufficient to treat the infection, disease, or symptoms thereof. The level or amount of the marker or biomarker (e.g., viral protein) determined in the method can be compared to known levels of the marker or biomarker in samples from healthy (uninfected), normal controls; in a pre-infection or pre-disease sample of the subject; or in other afflicted/infected/diseased patients to establish the treated subject's disease status. For monitoring, a second level or amount of the marker or biomarker in in a sample obtained from the subject is determined at a time point later than the determination of the first level or amount, and the two marker or biomarker levels or amounts can be compared to monitor the course of disease or infection, or the efficacy of the therapy/treatment. In certain embodiments, a pre-treatment level of the marker or biomarker in the subject (e.g., in a sample obtained from the subject) is determined prior to beginning treatment as described; this pre-treatment level of marker or biomarker can then be compared to the level of the marker or biomarker in the subject after the treatment commences and/or during the course of treatment to determine the efficacy of (monitor the efficacy of) the disease treatment. In the described methods, a subject may be a human subject or patient, or a non-human animal or veterinary subject.

The non-naturally occurring, broadly reactive influenza virus or IBV antigen polypeptides, such as H1, H2, H3, H5, or H7 influenza virus HA or NA polypeptides, or the IBV HA polypeptides, as described, and VLPs comprising such HA or NA polypeptides, or compositions thereof, can be administered to a subject by any of the routes normally used for introducing a recombinant protein, composition containing the recombinant protein, or recombinant virus into a subject. Routes and methods of administration include, without limitation, intradermal, intramuscular, intraperitoneal, intrathecal, parenteral, such as intravenous (IV) or subcutaneous (SC), vaginal, rectal, intranasal, inhalation, intraocular, intracranial, or oral. Parenteral administration, such as subcutaneous, intravenous or intramuscular administration, is generally achieved by injection (immunization). Injectables can be prepared in conventional forms and formulations, either as liquid solutions or suspensions, solid forms (e.g., lyophilized forms) suitable for solution or suspension in liquid prior to injection, or as emulsions. Injection solutions and suspensions can be prepared from sterile powders, granules, and tablets. Administration can be systemic or local.

The non-naturally occurring, broadly reactive influenza virus or IBV antigen polypeptides, such as H1, H2, H3, H5, or H7 influenza virus HA or NA polypeptides, or the IBV HA polypeptides, as described, and VLPs comprising such HA or NA polypeptides, or compositions thereof, can be administered in any suitable manner, such as with pharmaceutically acceptable carriers as described supra. Pharmaceutically acceptable carriers are determined in part by the particular immunogen or composition being administered, as well as by the particular method used to administer the composition. Accordingly, a pharmaceutical composition comprising the immunogenic non-naturally occurring influenza virus or IBV antigen polypeptides, such as H1, H2, H3, H5, or H7 influenza virus HA or NA polypeptides, or the IBV HA polypeptides, as described, and VLPs comprising such HA or NA polypeptides, or compositions thereof, can be prepared using a wide variety of suitable and physiologically and pharmaceutically acceptable formulations.

Administration of the broadly reactive, immunogenic virus antigen polypeptides, such as H1, H2, H3, H5, or H7 influenza virus HA or NA polypeptides, or the IBV HA polypeptides, as described, and VLPs comprising such HA or NA polypeptides, or compositions thereof, can be accomplished by single or multiple doses. The dose administered to a subject should be sufficient to induce a beneficial therapeutic response in a subject over time, such as to inhibit, block, reduce, ameliorate, protect against, or prevent disease or infection by influenza virus (e.g., H1, H2, H3, H5, or H7 influenza virus) or IBV. The dose required will vary from subject to subject depending on the species, age, weight and general condition of the subject, by the severity of the infection being treated, by the particular composition being used and by the mode of administration. An appropriate dose can be determined by a person skilled in the art, such as a clinician or medical practitioner, using only routine experimentation.

Further provided is a method of eliciting an immune response to influenza virus or IBV in a subject by administering to the subject a non-naturally occurring, broadly reactive H1, H2, H3, H5, or H7 influenza virus HA or NA polypeptide, or the IBV HA polypeptide, as described, or VLPs comprising such HA or NA polypeptides, compositions thereof, or fusion proteins containing the H1, H2, H3, H5, or H7 influenza virus HA or NA polypeptides, or the IBV HA polypeptides, as described herein. In some embodiments, the influenza virus or IBV protein (e.g., HA or NA protein), fusion protein, or VLP can be administered using any suitable route of administration, such as, for example, by intramuscular injection. In some embodiments, the influenza virus or IBV protein (e.g., HA or NA protein), fusion protein, or VLP is administered as a composition comprising a pharmaceutically acceptable carrier. In some embodiments the composition comprises an adjuvant selected from, for example, alum, Freund's complete or incomplete adjuvant, a biological adjuvant or immuno-stimulatory oligonucleotides (such as CpG oligonucleotides). In other embodiments, the composition may be administered in combination with another therapeutic agent or molecule.

Also provided is a method of immunizing a subject against infection or disease or the symptoms thereof caused by H1, H2, H3, H5, or H7 influenza virus, or by IBV, in which the method involves administering to the subject VLPs containing a non-naturally occurring, broadly reactive H1, H2, H3, H5, or H7 influenza HA or NA protein, a broadly reactive IBV HA protein, as described herein, or administering an immunogenic composition thereof. In some embodiments of the method, the composition further comprises a pharmaceutically acceptable carrier and/or an adjuvant. For example, the adjuvant can be alum, Freund's complete or incomplete adjuvant, a biological adjuvant or immuno-stimulatory oligonucleotides (such as CpG oligonucleotides). In an embodiment, the VLPs (or compositions thereof) are administered intramuscularly.

In some embodiments of the methods of eliciting an immune response or immunizing a subject against virus infection or disease caused by or associated with influenza virus (e.g., H1, H2, H3, H5, or H7 influenza), or IBV, the subject is administered at least 1 µg of the VLPs containing a non-naturally occurring, broadly reactive influenza virus (e.g., H1, H2, H3, H5, or H7 influenza) HA or NA protein, or IBV HA protein, such as at least 5 µg, at least 10 µg, at least 15 µg, at least 20 µg, at least 25 µg, at least 30 µg, at least 40 µg g or at least 50 µg of the VLPs containing the non-naturally occurring, broadly reactive influenza virus (e.g., H1, H2, H3, H5, or H7 influenza) HA or NA protein, or IBV HA protein, for example about 1 to about 50 µg or about 1 to about 25 µg of the VLPs containing the influenza virus (e.g., H1, H2, H3, H5, or H7 influenza) HA or NA protein, or IBV HA protein. In particular examples, the subject is administered about 5 to about 20 g of the VLPs, or about 10 to about 15 µg of the VLPs. In a specific, yet nonlimiting example, the subject is administered about 15 µg of the VLPs. However, one of skill in the art is capable of determining a therapeutically effective amount of VLPs (for example, an amount that provides a therapeutic effect or protection against influenza virus (e.g., H1, H2, H3, H5, or H7 influenza), or IBV, infection suitable for administering to a subject in need of treatment or protection from virus infection.

It is expected that the administration of VLPs comprising a non-naturally occurring, broadly reactive influenza virus HA or NA protein, or an IBV HA protein, as described herein will elicit high titers of neutralizing antibodies directed against the diverse repertoire of epitopic determinants on the HA or NA protein immunogen, as well as therapeutic or protective levels of HA-inhibiting (HAI) antibodies that are directed against a number of representative influenza or IBV isolates and will provide complete protection against lethal challenge with influenza virus (e.g., H1, H2, H3, H5, or H7 influenza) and/or related influenza virus types, or against lethal challenge with IBV. The VLPs containing a non-naturally occurring, broadly reactive influenza HA or NA protein (e.g., H1, H2, H3, H5, or H7 influenza HA or NA protein) as described herein, elicit a broader immune response (e.g., elicit neutralizing antibodies directed against a broader range of influenza virus isolates compared to the immune response elicited by, for example, a polyvalent influenza virus (e.g., a polyvalent H1, H2, H3, H5, or H7 influenza virus) vaccine. The VLPs containing a non-naturally occurring, broadly reactive IBV HA protein as described herein, elicit a broader immune response (e.g., elicit neutralizing antibodies directed against a broader range of IBV isolates compared to the immune response elicited by a known or standard IBV vaccine.

Adjuvants and Combination Therapies

The influenza virus immunogens or immunogenic compositions containing an influenza protein antigen (e.g., an H1, H2, H3, H5, or H7 influenza HA or NA antigen), or containing influenza virus (e.g., H1, H2, H3, H5, or H7 influenza virus) VLPs as described herein, can be administered alone or in combination with other therapeutic agents to enhance antigenicity or immunogenicity, i.e., to increase an immune response, such as the elicitation of specific antibodies, in a subject. Similarly, the IBV immunogens or immunogenic compositions containing an IBV protein antigen (e.g., IBV HA antigen), or containing IBV VLPs as described herein, can be administered alone or in combination with other therapeutic agents to enhance antigenicity or immunogenicity, i.e., to increase an immune response, such as the elicitation of specific antibodies, in a subject. By way of example, the H1, H2, H3, H5, or H7 influenza virus, or the IBV, VLPs can be administered with an adjuvant, such as alum, Freund's incomplete adjuvant, Freund's complete adjuvant, biological adjuvant, or immuno-stimulatory oligonucleotides (such as CpG oligonucleotides).

One or more cytokines, such as interleukin-1 (IL-2), interleukin-6 (IL-6), interleukin-12 (IL-12), the protein memory T-cell attractant "Regulated on Activation, Normal T Expressed and Secreted" (RANTES), granulocyte-macrophage-colony stimulating factor (GM-CSF), tumor necrosis factor-alpha (TNF-α), or interferon-gamma (IFN-γ); one or more growth factors, such as GM-CSF or granulocyte-colony stimulation factor (G-CSF); one or more molecules such as the TNF ligand superfamily member 4 ligand (OX40L) or the type 2 transmembrane glycoprotein receptor belonging to the TNF superfamily (4-1BBL), or combinations of these molecules, can be used as biological adjuvants, if desired or warranted (see, e.g., Salgaller et al., 1998, *J Surg. Oncol.* 68(2):122-38; Lotze et al., 2000, *Cancer J Sci. Am.* 6(Suppl 1):561-6; Cao et al., 1998, *Stem Cells* 16(Suppl 1):251-60; Kuiper et al., 2000, *Adv. Exp. Med. Biol.* 465:381-90). These molecules can be administered systemically (or locally) to a subject.

Several ways of inducing cellular responses, both in vitro and in vivo, are known and practiced in the art. Lipids have been identified as agents capable of assisting in priming cytotoxic lymphocytes (CTL) in vivo against various antigens. For example, palmitic acid residues can be attached to the alpha and epsilon amino groups of a lysine residue and then linked (for example, via one or more linking residues, such as glycine, glycine-glycine, serine, serine-serine, or the like) to an immunogenic peptide (U.S. Pat. No. 5,662,907). The lipidated peptide can then be injected directly in a micellar form, incorporated in a liposome, or emulsified in an adjuvant. As another example, *E. coli* lipoproteins, such as tripalmitoyl-S-glycerylcysteinlyseryl-serine can be used to prime tumor-specific CTL when covalently attached to an appropriate peptide (see, e.g., Deres et al., 1989, *Nature* 342:561). Moreover, the induction of neutralizing antibodies can also be primed with the same molecule conjugated to a peptide which displays an appropriate epitope, and two compositions can be combined to elicit both humoral and cell-mediated responses where such a combination is deemed desirable.

While treatment methods may involve the administration of VLPs containing a non-naturally occurring, broadly reactive HA or NA immunogenic protein as described herein, one skilled in the art will appreciate that the non-naturally occurring, broadly reactive HA or NA protein itself (in the absence of a viral particle), as a component of a pharmaceutically acceptable composition, or as a fusion protein, can be administered to a subject in need thereof to elicit an immune response in the subject.

Kits

Also provided are kits containing a non-naturally occurring, broadly reactive influenza virus or IBV immunogen as described, or a vaccine, or a pharmaceutically acceptable composition containing the immunogen and a pharmaceutically acceptable carrier, diluent, or excipient, for administering to a subject in need, for example. The immunogen may be in the form of an influenza virus (e.g., H1, H2, H3, H5, or H7 influenza virus) protein (polypeptide) or polynucleotide (a polynucleotide encoding an influenza virus protein), e.g., an H1, H2, H3, H5, or H7 influenza virus HA or NA protein, as described herein. The immunogen may be in the form of an IBV protein (polypeptide) or a polynucleotide (a polynucleotide encoding an IBV protein), e.g., IBV HA, as described herein. Kits containing one or more of the plasmids, or a collection of plasmids as described herein, are also provided. As will be appreciated by the skilled practitioner in the art, such a kit may contain one or more containers that house the immunogen, vaccine, or composition, diluents or excipients, as necessary, and instructions for use.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Useful techniques for particular embodiments will be discussed in the sections that follow.

EXAMPLES

The following examples are provided to illustrate certain particular features and/or embodiments. The examples should not be construed to limit the disclosure to the particular features or embodiments described.

Example 1

Hemagglutination-Inhibition (HAI) Assay

A hemagglutination inhibition (HAI) assay is used to assess functional antibodies to an HA or NA virus protein that are able to inhibit agglutination of guinea pig, horse, or turkey erythrocytes (red blood cells (RBCs)). The protocols are adapted from the WHO laboratory influenza surveillance manual (Gillim-Ross and Subbarao, 2006, *Cin Microbiol Rev* 19(4):614-636) and use the host-species that is frequently used to characterize contemporary H3N2 strains that have preferential binding to alpha (2, 6) linked sialic acid receptors. Turkey or guinea pig erythrocytes are used to compare whether there is a difference in HAI, depending on the type of erythrocyte used.

Sera used in the assay contain antibodies generated following immunization of animals (mice) with VLPs containing influenza virus (e.g., H1, H2, H3, H5, or H7 influenza virus), or IBV. HA protein sequences, e.g., the HA proteins of FIGS. 1A-1F (SEQ ID NOs: 1-6) and as shown supra, along with control, wild-type HA sequences, and/or PBS control. For immunization, 5 or more mice are used per group. Each animal receives 3 µg of the HA antigen/VLP as immunogen and squalene adjuvant (AF03) (MF Klucker, 2012, *J. Pharm. Sci.*, 101(12):4490-4500) per dose. A homologous prime, boost, boost immunization/administration regimen is employed. Mice are bled on day 77 following a boost with the immunogen on day 56.

To inactivate nonspecific inhibitors, sera are treated with receptor-destroying enzyme (RDE) (Denka Seiken, Co., Japan) prior to being tested. (Bright et al., 2005, *Lancet* 366(9492):1175-1181; Bright et al., 2003, *Virology* 308(2):270-278; Bright et al., 2006, *JAAIA* 295(8):891-894; Mitchell et al., 2004, *Vaccine* 21(9-10):902-914; Ross et al., 2000, *Nat Immunol* 1(2):127-131). Briefly, three parts of RDE are added to one part of sera and incubated overnight at 37° C.

RDE is inactivated by incubation at 56° C. for approximately 30 minutes (~30 min.). RDE-treated sera are diluted in a series of two-fold serial dilutions in v-bottom microtiter (multi-well) plates. An equal volume of each virus, adjusted to approximately 8 hemagglutination units (HAU)/50 µl, is added to each well. The plates are covered and incubated at room temperature for 20 minutes, followed by the addition of 0.8% guinea pig erythrocytes (Lampire Biologicals, Pipersville, PA, USA) in phosphate buffered saline (PBS). Red blood cells are stored at 4° C. and used within 72 hours of preparation.

The plates are mixed by agitation and covered, and the RBCs are allowed to settle for 1 hour at room temperature. The HAI titer is determined by the reciprocal dilution of the last well that contains non-agglutinated RBCs. Positive and negative serum controls are included for each plate. In general, all mice are negative (HAI ≤1:10) for preexisting antibodies to currently circulating viruses (e.g., human influenza virus or IBV) prior to vaccination. Seroprotection is defined as HAI titer >1:40, and seroconversion is defined as a 4-fold increase in titer compared to baseline, as per the WHO and European Committee for Medicinal Products to evaluate influenza vaccines. A more stringent threshold of >1:80 is often examined. Because mice are naïve and seronegative at the time of vaccination, seroconversion and seroprotection rates are interchangeable in the experiments.

Example 2

Enzyme-Linked Lectin Assay (ELLA)

To determine the amount of neuraminidase (NA) inhibiting antibodies present in a sample, such as in immunized animal sera, an enzyme-linked lectin assay (ELLA) is performed as described by L. Couzens et al., 2014. *J Virol. Methods*, Vol. 210, pp. 7-14). Briefly, flat-bottom, Maxisorp polystyrene 96-well plates (Maxisorp, Nunc) are coated with fetuin (100 pL; Sigma-Aldrich) at 25 µg/ml at 4° C. overnight. Serum samples are heat-treated at 56° C. for 1 hour prior to serial two-fold dilutions in PBS and subsequent co-incubation with a predetermined 90% NA activity at 37° C. for 16-18 hours. After three wash steps with PBS containing 0.05% Tween-20 (PBS-T), peroxidase-labeled lectin from *Arachis hypogaea* (Sigma-Aldrich) is added, and the samples are incubated for 2 hours at room temperature in the dark. Plates are washed again before adding o-phenylene-diamine dihydrochloride (OPD) substrate (Sigma-Aldrich). The reaction is stopped with 1N sulfuric acid before reading the absorbance at 492 nm. The sialidase-inhibiting antibody titer is expressed as the reciprocal of the highest dilution that exhibited >50% inhibition of NA activity.

Example 3

Virus-Like Particle (Vaccine) Preparation

Mammalian 293T cells are transfected with each of three mammalian expression plasmids expressing either the influenza neuraminidase (e.g., A/mallard/Alberta/24/01, H7N3), the HIV p55 gag sequences, or other control expression plasmids containing a polynucleotide sequence encoding an HA, HA1, HA2, or NA protein, using methods practiced by those having skill in the art (see, e.g., U.S. Patent Application Publication 2015/0030628). Following 72 hours of incubation at 37° C., supernatants from transiently transfected cells are collected, centrifuged to remove cellular debris, and filtered through a 0.22 µm pore membrane. Mammalian virus-like particles (VLPs) are purified and sedimented by ultracentrifugation on a 20% glycerol cushion at 135,000×g for 4 hours at 4° C. VLPs are resuspended in phosphate buffered saline (PBS) and total protein concentration is assessed using a conventional bicinchoninic acid assay (BCA). The hemagglutination activity of each preparation of VLPs is determined by adding an equal volume of turkey red blood cells (RBCs) to a V-bottom 96-well plate and incubating with serially-diluted volumes of VLPs for 30 minutes at room temperature (RT). The highest dilution of VLP with full agglutination of RBCs is considered the endpoint HA titer.

Example 4

Determination of HA Content by Enzyme Linked Immunosorbent Assay (ELISA)

A high-affinity, 96-well, flat-bottom ELISA plate is coated with 5-10 μg of total protein of VLPs, and serial dilutions of a recombinant influenza virus antigen (e.g., 3006_H3_Vc, Protein Sciences, Meriden, CT) in ELISA carbonate buffer (50 mM carbonate buffer, pH 9.5) are added to the wells. The plate is incubated overnight at 4° C. on a rocker. The next morning, the plates are washed in PBS with 0.05% Tween-20 (PBST), and non-specific epitopes are blocked with 1% bovine serum albumin (BSA) in PBST solution for 1 hour at RT. The buffer is removed, and stalk-specific Group 2 monoclonal antibody CR8020 (Tharakaraman, K. et al., 2014, Cell Host & Microbe, Vol. 15, pp. 644-651; Ekiert, D. C. et al., 2012, Science, 333(6044):843-850; Creative Biolabs, Shirley, NY) is added to plate, followed by a 1-hour incubation at 37° C. The plates are washed and then are probed with goat anti-human IgG horseradish-peroxidase-conjugated secondary antibody (2040-05, Southern Biotech, Birmingham, AL) for 1 hour at 37° C.

Following incubation with secondary antibody, the plates are washed. Freshly prepared o-phenylenediamine dihydrochloride (OPD) (P8287, Sigma, City, State, USA) substrate in citrate buffer (P4922, Sigma) is then added to wells, followed by the addition of 1N $H_2SO_4$ stopping reagent. The plates are read at 492 nm absorbance using a microplate reader (Powerwave XS, Biotek, Winooski, VT). Background signal is subtracted from negative wells. Linear regression standard curve analysis is performed using the known concentrations of recombinant standard antigen to estimate the HA content in lots of VLPs.

Example 5

Generation of HA Immunogens that Elicit Broadly Reactive Antisera in Immunized Mice The hemagglutination inhibition (HAI) assay described above (Example 1) is used to assess functional antibodies to the HA protein that are generated in mice following immunization with VLPs expressing each of the influenza virus or IBV HA antigens (e.g., FIGS. TA-1F (SEQ ID NOs: 1-6)). BALB/c mice (e.g., 8 mice per immunogen tested) are immunized with VLPs expressing the respective HA antigens. The sera from each mouse are collected and assessed in the HAI assay. All virus strains tested against the sera in the HAI assay are presented on the x-axes of graphs generated from the assay. Antisera titers may range, for example, from 1:40-1:80. A titer of 1:40 is considered to provide the minimal protection in humans for seasonal influenza. The HAI assay results indicate whether, following immunization, the HA protein immunogens generate broadly reactive antisera that effectively neutralize HA from a variety of virus strains as well as, or better than, antisera from animals immunized with control wild-type virus that typically produces high titer antisera in animals following immunization.

Example 6

Mouse Studies

BALB/c mice (Mus musculus, females, 6 to 8 weeks old) are purchased from Jackson Laboratory (Bar Harbor, ME, USA), housed in microisolator units and allowed free access to food and water. The animals are cared for under University of Georgia Research Animal Resources guidelines for laboratory animals. All procedures are reviewed and approved by the Institutional Animal Care and Use Committee (IACUC). Mice (5 or 10 mice per group) are administered (vaccinated with) purified virus-like particles (VLPs), (3.0 μg/mouse), based upon HA content from ELISA quantification, and VLP vaccines are delivered to the animals via intramuscular injection at week 0. A prime-boost boost regimen for VLP administration is used. Animals are boosted with the same vaccine at the same dose at weeks 4 and 8. Vaccines at each dose are formulated with an emulsified squalene-in-water adjuvant (Sanofi Pasteur, Lyon, France). The final concentration after mixing 1:1 with VLPs is 2.5% squalene. Twenty-eight days after each vaccination, blood samples are collected via the submandibular cheek, and the samples are transferred to a microcentrifuge tube. The tubes are centrifuged at 10,000 rpm for 10 minutes. Serum samples are removed and frozen at −20° C.±5° C. Results of a prime-boost challenge using different NA immunogens as VLPs administered to mice are determined.

Example 7

Ferret Studies

Fitch ferrets (Mustela putorius faro, female, 6-12-months of age), influenza naïve and de-scented, are purchased from Marshall Farms (Sayre, Pa., USA). Ferrets are pair-housed in stainless steel cages (Shor-line, Kansas City, Kans., USA) containing Sani-chips Laboratory Animal Bedding (P.J. Murphy Forest Products, Montville, N.J., USA). Ferrets are provided with Teklad Global Ferret Diet (Harlan Teklad, Madison, Wis., USA) and fresh water ad libitum.

Purified VLPs are diluted in PBS, pH 7.2, to achieve final concentration. Ferrets (n=3) are vaccinated with 15 μg of purified VLPs, based upon HA content as determined by densitometry assay, via intramuscular injection in the quadriceps muscle in a volume of 0.25 ml at week 0, and then are boosted with the same dose at week 3. Immunogen vaccines are stored at −80° C. prior to use and formulated with IMJECT® alum adjuvant (IMJECT® Alum; Pierce Biotechnology, Rockford, IL USA) or with the above-described emulsified squalene-in-water adjuvant immediately prior to use. Animals are monitored for adverse events, including weight loss, temperature, loss of activity, nasal discharge, sneezing and diarrhea weekly during the vaccination regimen. Prior to vaccination, animals are confirmed by HAI assay to be seronegative for circulating influenza A (e.g., H1N1) and influenza B viruses. Fourteen to twenty-one days after each vaccination, blood is collected from anesthetized ferrets via the anterior vena cava and transferred to a microfuge tube. The tubes are centrifuged; serum is removed and frozen at −20±5° C.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any 5 single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A non-naturally occurring and immunogenic influenza virus antigen, which comprises or consists of the amino acid sequence of a hemagglutinin (HA) antigen as set forth in SEQ ID NO: 1.

2. The influenza virus antigen of claim 1, wherein the influenza virus is an H1 influenza virus.

3. A non-naturally occurring and immunogenic influenza virus antigen, which comprises or consists of the amino acid sequence of a neuraminidase (NA) antigen as set forth in SEQ ID NO: 8.

4. The influenza virus antigen of claim 3, wherein the NA antigen is an N2 NA-A antigen.

5. A virus-like particle (VLP) comprising the influenza virus HA antigen of claim 1.

6. The VLP of claim 5, which comprises a polynucleotide encoding the influenza virus HA antigen.

7. A non-naturally occurring immunogen capable of generating an immune response against present and future influenza virus strains; wherein the immunogen comprises or consists of the amino acid sequence of a hemagglutinin (HA) antigen as set forth in SEQ ID NO: 1, and/or wherein the immunogen comprises or consists of the amino acid sequence of a neuraminidase (NA) antigen as set forth in SEQ ID NO: 8.

8. The immunogen of claim 7, wherein the immune response comprises the production of neutralizing antibodies and/or the production of T lymphocytes.

9. The immunogen of claim 7, wherein the immune response comprises the production of antibodies having hemagglutinin inhibitory activity and/or neuraminidase inhibitory activity.

10. A pharmaceutically acceptable composition comprising the virus antigen of claim 1 and a pharmaceutically acceptable carrier, diluent, or excipient.

11. An immunogenic composition or vaccine comprising the virus antigen of claim 1.

12. A pharmaceutically acceptable composition comprising the immunogenic composition or vaccine of claim 11 and a pharmaceutically acceptable carrier, diluent, or excipient.

13. A method of generating an immune response in a subject, the method comprising administering to the subject an effective amount of the pharmaceutically acceptable composition of claim 12.

14. The method of claim 13, wherein the subject is a human subject.

15. An isolated polynucleotide encoding the virus antigen of claim 1.

16. A composition comprising the isolated polynucleotide of claim 15 and a pharmaceutically acceptable carrier, diluent, or excipient.

17. A virus-like particle (VLP) comprising the polynucleotide of claim 15.

18. The immunogen of claim 7, wherein the immune response comprises the production of antibodies having neuraminidase inhibitory activity.

19. A pharmaceutically acceptable composition comprising the VLP of claim 5 and a pharmaceutically acceptable carrier, diluent, or excipient.

20. A pharmaceutically acceptable composition comprising the immunogen of claim 7 and a pharmaceutically acceptable carrier, diluent, or excipient.

21. The influenza virus antigen of claim 1, which is a recombinant or synthetic antigen.

22. The immunogen of claim 7, which is recombinant or synthetic.

23. A virus-like particle (VLP) comprising the influenza virus NA antigen of claim 3.

24. The VLP of claim 23, which comprises a polynucle-otide encoding the influenza virus NA antigen.

25. A pharmaceutically acceptable composition compris-ing the virus antigen of claim 3 and a pharmaceutically acceptable carrier, diluent, or excipient.

26. An immunogenic composition or vaccine comprising the virus antigen of claim 3.

27. A pharmaceutically acceptable composition compris-ing the immunogenic composition or vaccine of claim 26 and a pharmaceutically acceptable carrier, diluent, or excipi-ent.

28. An isolated polynucleotide encoding the virus antigen of claim 3.

29. A composition comprising the isolated polynucleotide of claim 28 and a pharmaceutically acceptable carrier, diluent, or excipient.

30. A virus-like particle (VLP) comprising the polynucle-otide of claim 28.

31. A pharmaceutically acceptable composition compris-ing the VLP of claim 30 and a pharmaceutically acceptable carrier, diluent, or excipient.

32. The influenza virus antigen of claim 3, which is a recombinant or synthetic antigen.

33. A method of generating an immune response in a subject, the method comprising administering to the subject an effective amount of the pharmaceutically acceptable composition of claim 25.

34. The method of claim 33, wherein the subject is a human subject.

\* \* \* \* \*